(12) United States Patent
Bertin et al.

(10) Patent No.: US 11,376,321 B2
(45) Date of Patent: Jul. 5, 2022

(54) METHOD FOR REMOVING ANTI-AAV ANTIBODIES FROM A BLOOD-DERIVED COMPOSITION

(71) Applicants: GENETHON, Evry (FR); INSERM (INSTITUT NATIONAL DE LA SANTE ET DE LA RECHERCHE MEDICALE), Paris (FR); SORBONNE UNIVERSITÉ, Paris (FR); ASSOCIATION INSTITUT DE MYOLOGIE, Paris (FR)

(72) Inventors: Bérangére Bertin, Vanves (FR); Carole Masurier, Perigny-sur-Yerres (FR); Otto-Wilhelm Merten, Crespieres (FR); Federico Mingozzi, Paris (FR)

(73) Assignees: GENETHON, Evry (FR); INSERM (INSTITUT NATIONAL DE LA SANTE ET DE LA RECHERCHE MEDICALE), Paris (FR); SORBONNE UNIVERSITÉ, Paris (FR); ASSOCIATION INSTITUT DE MYOLOGIE, Paris (FR)

( * ) Notice: Subject to any disclaimer, the term of this patent is extended or adjusted under 35 U.S.C. 154(b) by 0 days.

(21) Appl. No.: 16/490,181

(22) PCT Filed: Mar. 1, 2018

(86) PCT No.: PCT/EP2018/055108
§ 371 (c)(1),
(2) Date: Aug. 30, 2019

(87) PCT Pub. No.: WO2018/158397
PCT Pub. Date: Sep. 7, 2018

(65) Prior Publication Data
US 2020/0069790 A1  Mar. 5, 2020

(30) Foreign Application Priority Data
Mar. 2, 2017  (EP) .................................. 17305228

(51) Int. Cl.
| | | |
|---|---|---|
| *A61K 39/235* | (2006.01) | |
| *A61M 1/36* | (2006.01) | |
| *C07K 16/06* | (2006.01) | |
| *C07K 16/08* | (2006.01) | |
| *C12N 7/00* | (2006.01) | |

(52) U.S. Cl.
CPC ......... *A61K 39/235* (2013.01); *A61M 1/3687* (2013.01); *C07K 16/065* (2013.01); *C07K 16/081* (2013.01); *C12N 7/00* (2013.01); *C12N 2710/10032* (2013.01); *C12N 2710/10041* (2013.01)

(58) Field of Classification Search
CPC . A61K 39/235; A61M 1/3687; A61M 1/3486; C07K 16/065; C07K 16/081; C12N 7/00; C12N 2710/10032; C12N 2710/10041; C12N 2750/14141; C12N 15/86
See application file for complete search history.

(56) References Cited

U.S. PATENT DOCUMENTS

| | | | | |
|---|---|---|---|---|
| 5,122,112 A | * | 6/1992 | Jones ................... | G01N 33/564 |
| | | | | 210/502.1 |
| 5,869,047 A | * | 2/1999 | Blake ................... | C07K 14/315 |
| | | | | 424/140.1 |

FOREIGN PATENT DOCUMENTS

WO     WO 00/20041        4/2000

OTHER PUBLICATIONS

Raper SE, Wilson JM, Nunes FA. Flushing out antibodies to make AAV gene therapy available to more patients. Mol Ther. Feb. 2013;21(2):269-71.*
Louis Jeune V, Joergensen JA, Hajjar RJ, Weber T. Pre-existing anti-adeno-associated virus antibodies as a challenge in AAV gene therapy. Hum Gene Ther Methods. Apr. 2013;24(2):59-67. Epub Apr. 3, 2013.*
Mimuro J, Mizukami H, Hishikawa S, Ikemoto T, Ishiwata A, Sakata A, Ohmori T, Madoiwa S, Ono F, Ozawa K, Sakata Y. Minimizing the inhibitory effect of neutralizing antibody for efficient gene expression in the liver with adeno-associated virus 8 vectors. Mol Ther. Feb. 2013;21(2):318-23. Epub Dec. 18, 2012.*
Chicoine LG, Montgomery CL, Bremer WG, Shontz KM, Griffin DA, Heller KN, Lewis S, Malik V, Grose WE, Shilling CJ, Campbell KJ, et. al. Plasmapheresis eliminates the negative impact of AAV antibodies on microdystrophin gene expression following vascular delivery. Mol Ther. Feb. 2014;22(2):338-347. (Year: 2014).*
Wobus CE, Hügle-Dörr B, Girod A, Petersen G, et. al. Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000;74(19):9281-93. (Year: 2000).*
Buchwalow I, Samoilova V, Boecker W, Tiemann M. Non-specific binding of antibodies in immunohistochemistry: fallacies and facts. Sci Rep. 2011;1:28. Epub Jul. 1, 2011. (Year: 2011).*
Everest Biotech. "Non-specific binding, background and noise." https://everestbiotech.com/non-specific-binding-background-and-noise/; Accessed May 26, 2021. (Year: 2021).*
Martino AT, Herzog RW, Anegon I, Adjali O. Measuring immune responses to recombinant AAV gene transfer. Methods Mol Biol. 2011,807:259-72 (Year: 2011).*
Ito T, Yamamoto S, Hayashi T, Kodera M, Mizukami H, Ozawa K, Muramatsu S. A convenient enzyme-linked immunosorbent assay for rapid screening of anti-adeno-associated virus neutralizing antibodies. Ann Clin Biochem. Nov. 2009;46(Pt 6):508-10. Epub Sep. 3, 2009. (Year: 2009).*

(Continued)

*Primary Examiner* — Rachel B Gill
(74) *Attorney, Agent, or Firm* — Saliwanchik, Lloyd & Eisenschenk

(57) ABSTRACT

The present invention relates to a method for removing undesired anti-AAV antibodies from a blood-derived composition.

17 Claims, 14 Drawing Sheets

Figure 1:
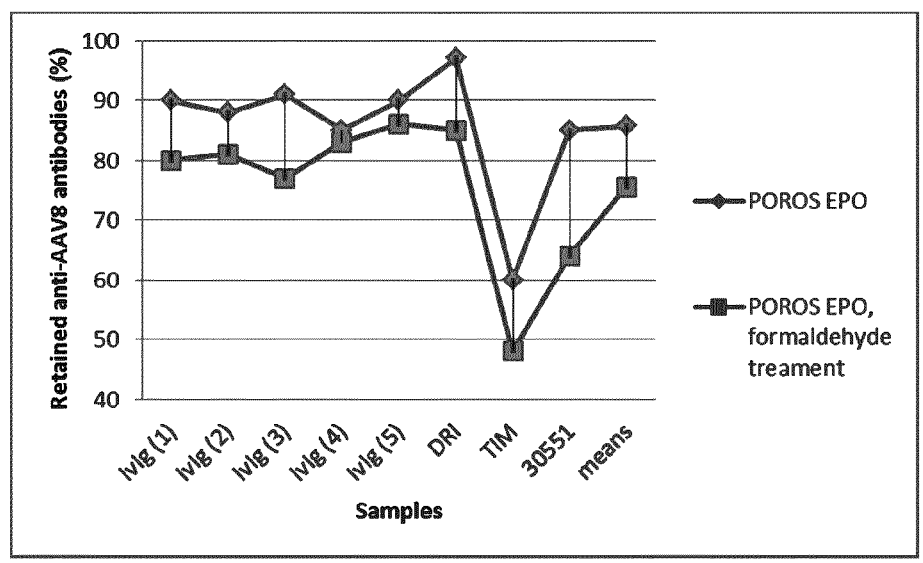

Specification includes a Sequence Listing.

(56) References Cited

OTHER PUBLICATIONS

Du P, Brendle S, Milici J, Camacho F, Zurlo J, Christensen N, Meyers C. Comparisons of VLP-Based ELISA, Neutralization Assays with Native HPV, and Neutralization Assays with PsV in Detecting HPV Antibody Responses in HIV-Infected Women. J AIDS Clin Res. Mar. 2015;6(3):433. (Year: 2015).*

Chicoine, L.G. et al. "Plasmapheresis Eliminates the Negative Impact of AAV Antibodies on Microdystrophin Gene Expression Following Vascular Delivery" *Molecular Therapy*, Feb. 2014, pp. 338-347, vol. 22, No. 2.

Masat, E. et al. "Humored Immunity to AAV Vectors in Gene Therapy: Challenges and Potential Solutions" *Discovery Medicine*, Jun. 2013, pp. 379-389, vol. 15, No. 85.

Monteilhet, V. et al. "A 10 Patient Case Report on the Impact of Plasmapheresis Upon Neutralizing Factors Against Adeno-associated Virus (AAV) Types 1, 2, 6, and 8" *Molecular Therapy*, Nov. 2011, pp. 2084-2091, vol. 19, No. 11.

Murphy, S. L. et al. "Prolonged Susceptibility to Antibody-mediated Neutralization for Adeno-associated Vectors Targeted to the Liver" *Molecular Therapy*, Jan. 2008, pp. 138-145, vol. 16, No. 1.

Written Opinion in International Application No. PCT/EP2018/055108, dated May 4, 2018, pp. 1-7.

\* cited by examiner

SEQUENCE LISTING

```
<160> NUMBER OF SEQ ID NOS: 3

<210> SEQ ID NO 1
<211> LENGTH: 22
<212> TYPE: DNA
<213> ORGANISM: artificial
<220> FEATURE:
<223> OTHER INFORMATION: qPCR forward primer

<400> SEQUENCE: 1
aagtcggtcc caaaatggta ga                                            22

<210> SEQ ID NO 2
<211> LENGTH: 18
<212> TYPE: DNA
<213> ORGANISM: artificial
<220> FEATURE:
<223> OTHER INFORMATION: qPCR reverse primer

<400> SEQUENCE: 2
tgccgtcgtt ggagttga                                                 18

<210> SEQ ID NO 3
<211> LENGTH: 18
<212> TYPE: DNA
<213> ORGANISM: artificial
<220> FEATURE:
<223> OTHER INFORMATION: qPCR probe

<400> SEQUENCE: 3
cagaatcaac agtttcag                                                 18
```

METHOD FOR REMOVING ANTI-AAV ANTIBODIES FROM A BLOOD-DERIVED COMPOSITION

CROSS-REFERENCE TO RELATED APPLICATION

This application is the U.S. national stage application of International Patent Application No. PCT/EP2018/055108, filed Mar. 1, 2018.

The Sequence Listing for this application is labeled "Seq-List.txt" which was created on Aug. 8, 2019 and is 1 KB. The entire content of the sequence listing is incorporated herein by reference in its entirety.

FIELD OF THE INVENTION

The present invention relates to a method for removing undesired anti-AAV neutralizing antibodies, from a blood-derived composition.

BACKGROUND OF THE INVENTION

The goal of genetic therapies for inherited diseases is the long-term correction of the disease phenotype in affected patients. Several clinical studies document the therapeutic potential of the approach in attaining this goal (Bainbridge et al., 2008, N Engl J Med 358(21):2231-2239; Cartier et al., 2009, Science 326(5954):818-823; Cideciyan et al., 2008, Proc Natl Acad Sci USA 105(39):15112-15117; Maguire et al., 2008, N Engl J Med 358(21):2240-2248; Nathwani et al., 2011, N Engl J Med 365(25):2357-2365).

Experience with in vivo administration of adeno-associated virus (AAV) vectors in human trials has led to some of the most exciting results in the field of gene therapy (Mingozzi and High, 2011, Current Gene Therapy, 11, 321-330). However, some of the limitations of the approach, not entirely identified in preclinical studies, became obvious in clinical studies. In particular, it is clear that the host immune system represents one of the most important obstacles to be overcome in terms of both safety and efficacy of gene transfer in vivo with AAV vectors (Mingozzi and High, 2013, Blood; 122(1):23-36).

It is now evident that anti-AAV neutralizing antibodies (NAbs) can completely prevent transduction of a target tissue, resulting in lack of efficacy, particularly when the vector is administered directly into the bloodstream (Masat, Pavani, Mingozzi, 2013, Discov Med. 2013, 15(85):379-89). Anti-AAV NAbs are highly prevalent in humans, and the frequency of subjects with detectable titers can reach up to two thirds of the population. The approach to the problem of preexisting humoral immunity to AAV so far has been the exclusion of seropositive subjects from enrollment in gene therapy clinical trials, but this solution is far from being optimal. Several additional strategies, such as plasmapheresis and transient immunosuppression, have been proposed and tested in a variety of preclinical animal models. The major drawback of plasmapheresis is that it may result in the total removal of circulating immunoglobulins, which leads to immunodeficiency requiring supplementation with purified intravenous immunoglobulins (IVIG). Aside from the obvious risk to contract infections due to the lack of protective humoral immunity, IVIG infusion is not recommended in gene transfer with AAV vectors, as IVIG preparations themselves may contain anti-AAV antibodies therein, thereby potentially reintroducing anti-AAV NAbs into the blood of the patient.

With respect to transient immunosuppression, one potential advantage when used in the context of AAV gene transfer is that, differently from organ transplant or autoimmune disease, the duration of the intervention in gene transfer would be relatively short, in the range of few hours (Murphy et al., 2008, Mol. Ther., 16(1):138-145) but one major limitation to the use of immunosuppression to achieve the complete eradication of anti-AAV antibodies is the lack of antigen specificity of the approach, which raises concerns over the risk of serious infections (Ginzler et al., 2012, Arthritis Res Ther, 14(1):R33) and malignancies.

Therefore, a need still exists to provide a strategy for removing specifically anti-AAV antibodies, such as anti-AAV NAbs, from a blood-derived composition that would be both reliable and safe for the patient.

SUMMARY OF THE INVENTION

In a first aspect, the invention relates to a method for removing anti-AAV antibodies, preferably anti-AAV neutralizing antibodies, from a blood-derived composition, comprising contacting said blood-derived composition with at least one support onto which one or more affinity ligand(s) specific of anti-AAV antibodies is bound. The method may be implemented in vitro or extracorporeally (i.e. ex vivo), as will be provided in details below.

In a particular embodiment, said one or more affinity ligand is an antigenic affinity ligand such as an AAV particle (either full or empty), an AAV capsid protein (or a fragment thereof), or a capsid peptide mimic of one or more serotypes. In a further particular embodiment, the AAV particle is an empty AAV particle. In another embodiment, the composition may be contacted with more than one support, wherein each support may have different affinity ligands specific of different AAV serotypes bound thereon.

The affinity ligand may be specific of an AAV serotype which is the serotype of an AAV gene therapy vector intended to be used in a subject in need thereof, and wherein the blood-derived composition is either from said subject, or is intended to be administered to said subject. Illustrative affinity ligands include those specific of serotype AAV-1, -2, -3, -4, -5, -6, -7, -8, -9, -10 (such as -cy10 or -rh10), -11, -rh74 or engineered AAV capsid variants such as AAV-2i8, AAV2G9, -LK3, -DJ, and -Anc80. In a particular embodiment, an affinity ligand specific of AAV8 is used.

In a particular embodiment, the method of the invention comprises contacting the blood-derived composition with a support onto which are bound a first affinity ligand specific of a first AAV serotype (for example specific of the AAV2 serotype) and a second affinity ligand specific of a second AAV serotype (for example specific of the AAV8 serotype). In a further particular embodiment, more than two affinity ligands, providing specificity for more than two AAV serotypes, are bound onto the support.

In a particular embodiment, the method of the invention comprises contacting the blood-derived composition with at least:
  one support onto which an affinity ligand specific of a first AAV serotype (for example specific of the AAV2 serotype) is bound, or on which a set of affinity ligands specific of said first AAV serotype, are bound; and
  one support on which an affinity ligand specific of a second AAV serotype (for example specific of the AAV8 serotype) is bound, or on which a set of affinity ligand specific of said second AAV serotype, are bound.

In a further embodiment, more than two supports are implemented, wherein each additional support may comprises bound thereon at least one additional affinity ligand specific for at least one additional AAV serotype.

In another embodiment, two or more supports are used, each comprising one or more affinity ligand(s) bound thereon, specific of one or more AAV serotypes. For example, a first support may be used onto which an affinity ligand specific of a first AAV serotype is bound, and a second support is used onto which an affinity ligand specific of a second AAV serotype and an affinity ligand specific of a third AAV serotype are bound. In an alternative example, a first support may be used onto which an affinity ligand specific of a first AAV serotype and an affinity ligand specific of a second AAV serotype are bound, and a second support is used onto which an affinity ligand specific of a third AAV serotype (and optionally one or more affinity ligand(s) specific of one or more additional AAV serotype(s), respectively) is bound.

The blood-derived composition submitted to the method of the invention may be, in particular whole blood, blood plasma, blood plasma fractions, blood plasma precipitate (e.g., cryoprecipitate, ethanol precipitate or polyethylene glycol precipitate), blood plasma supernatant (e.g., cryosupernatant, ethanol supernatant or polyethylene glycol supernatant), solvent/detergent (SD) plasma, platelets, intravenous immunoglobulin (IVIG), IgM, purified coagulation factor concentrate, fibrinogen concentrate, or various other compositions which are derived from human or animal. In a particular embodiment, the blood-derived composition is whole blood or an IVIG composition.

In a further embodiment, the blood-derived composition is loaded several times onto the same support (for example 2, 3, 4 or 5 times or more than 5 times) and/or the composition is loaded on several different columns serially arranged, either grafted with the same or different affinity ligand(s).

Another aspect of the invention relates to a composition obtainable by applying the method described above on a blood-derived composition. The composition of the invention is therefore a blood-derived composition deprived in anti-AAV antibodies. As mentioned, the blood-derived composition may in particular be whole blood, blood plasma, blood plasma fractions, blood plasma precipitate (e.g., cryoprecipitate, ethanol precipitate or polyethylene glycol precipitate), blood plasma supernatant (e.g., cryosupernatant, ethanol supernatant or polyethylene glycol supernatant), solvent/detergent (SD) plasma, platelets, intravenous immunoglobulin (IVIG), IgM, purified coagulation factor concentrate, fibrinogen concentrate, or various other compositions which are derived from human or animal. In a particular embodiment, the blood-derived composition is whole blood or an IVIG composition.

A further aspect of the invention relates to a support onto which one or more affinity ligand specific of one or more anti-AAV antibody, respectively, is grafted. The grafted affinity ligand(s) may be an antigenic affinity ligand such as an AAV particle (either empty or full), an AAV capsid protein, or fragments thereof, or a capsid peptide mimic of one or more serotypes, more particularly an AAV particle, even more particularly an empty AAV particle. The support may in particular be a poros or sepharose support, such as a sepharose support grafted with the affinity ligand via a NHS functional group. In particular embodiment, the support according to the invention is grafted with a first affinity ligand specific of a first AAV serotype, such as (empty or full) AAV8 particles or AAV8 capsid proteins, a second affinity ligand specific of a second AAV serotype such as (empty or full) AAV2 particles or AAV2 capsid proteins, or the first affinity ligand specific of the first AAV serotype and the second affinity ligand specific of the second AAV serotype (such as with (empty or full) AAV2 and (empty or full) AAV8 particles, or with AAV2 and AAV8 capsid proteins.

The invention further relates, in another aspect, to an AAV vector for use in a method for the treatment of a disease by gene therapy, wherein the AAV vector comprises a therapeutic gene of interest appropriate for the treatment of said disease, wherein said AAV vector is of a given serotype, wherein said AAV vector is for administration to a subject in need thereof after administration to said subject of a blood-derived composition which has been processed according to the method described above to remove anti-AAV antibodies specific of said given serotype from said composition.

In a particular embodiment, the blood-derived composition is whole blood or wherein the subject had previously undergone plasmapheresis and the blood-derived composition is an IVIG composition.

LEGENDS OF THE FIGURES

FIG. 1. Percentage of retained anti-AAV8 antibodies using POROS affinity columns to which $3.7 \times 10^{11}$ vg of AAV8 have been grafted. The grafted AAV particles were either crosslinked by a formaldehyde treatment or not.

Figure 2:
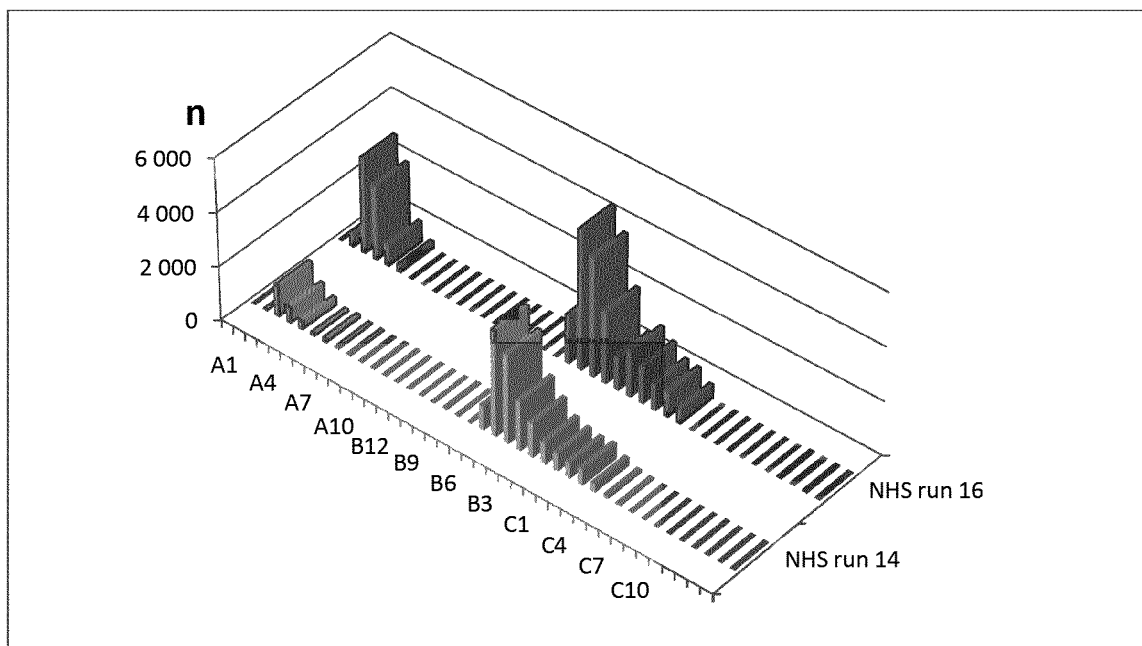

FIG. 2. Passage of IVIG samples over AAV8 columns and removal of anti-AAV8 antibodies (n=2) (flow rate: 0.25 ml/min, $3.4 \times 10^{12}$ vg of AAV8 grafted to a 5 mlNHS-sepharose column, 36 mg of IVIG loaded to the column) Notes: x-axis indicates the fractions (A1-B8: loading of the column followed by washing; B7-C2: elution using a citrate buffer step; C3-C12: reconditioning of the column); z-axis: ng of anti-AAV8.

Figure 3:
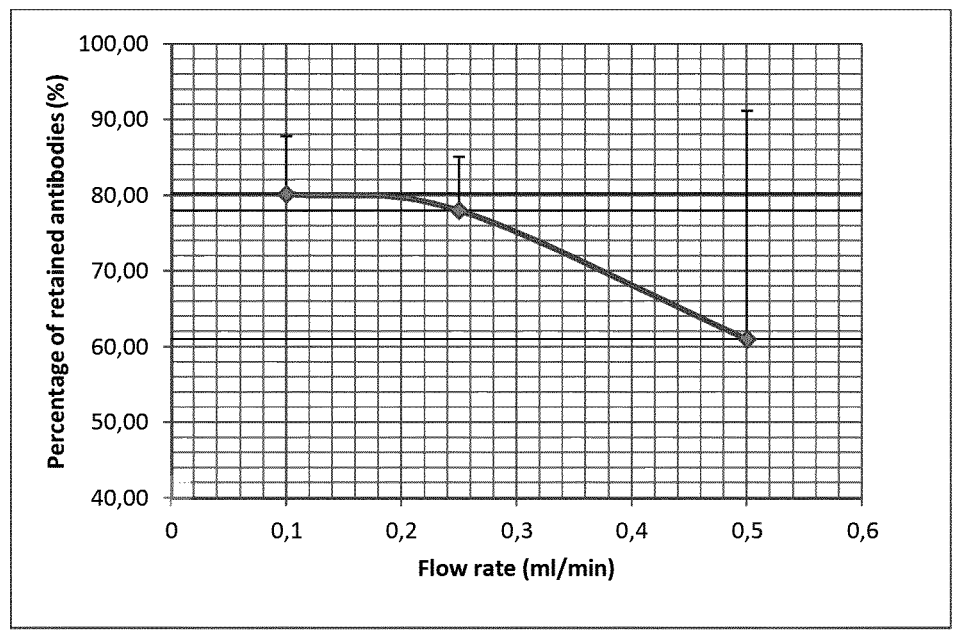

FIG. 3. Effect of flow rate on retention/removal of anti-AAV8 antibodies by a 5 ml AAV8-NHS-sepharose column (loading: 36 or 72 mg of IVIG; flow 0.1 ml/min (n=5), flow 0.25 ml/min (n=2), flow 0.5 ml/min (n=4), the bars indicate SD).

Figure 4:
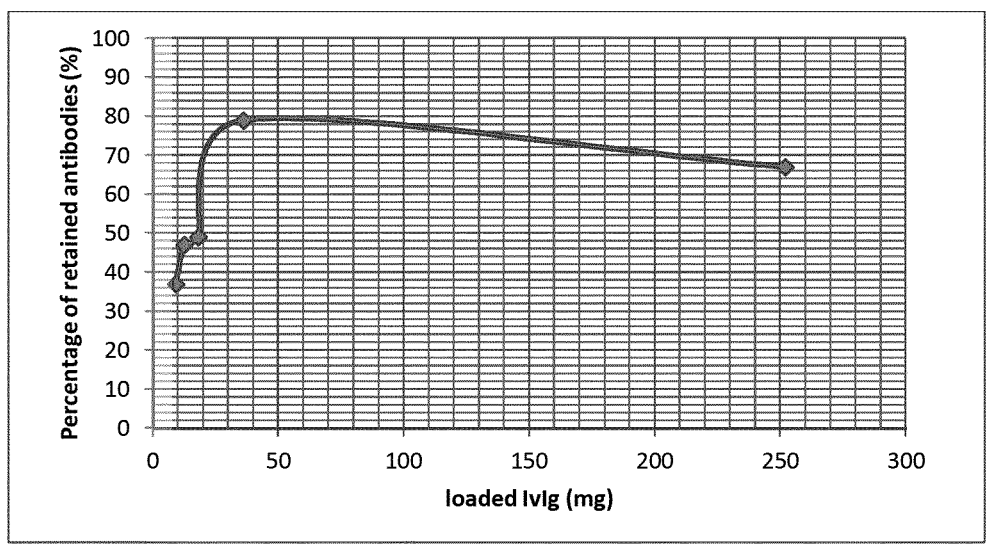

FIG. 4. Effect of anti-AAV8 antibody retention (%) in terms of the quantity of loaded sample.

Figure 5:
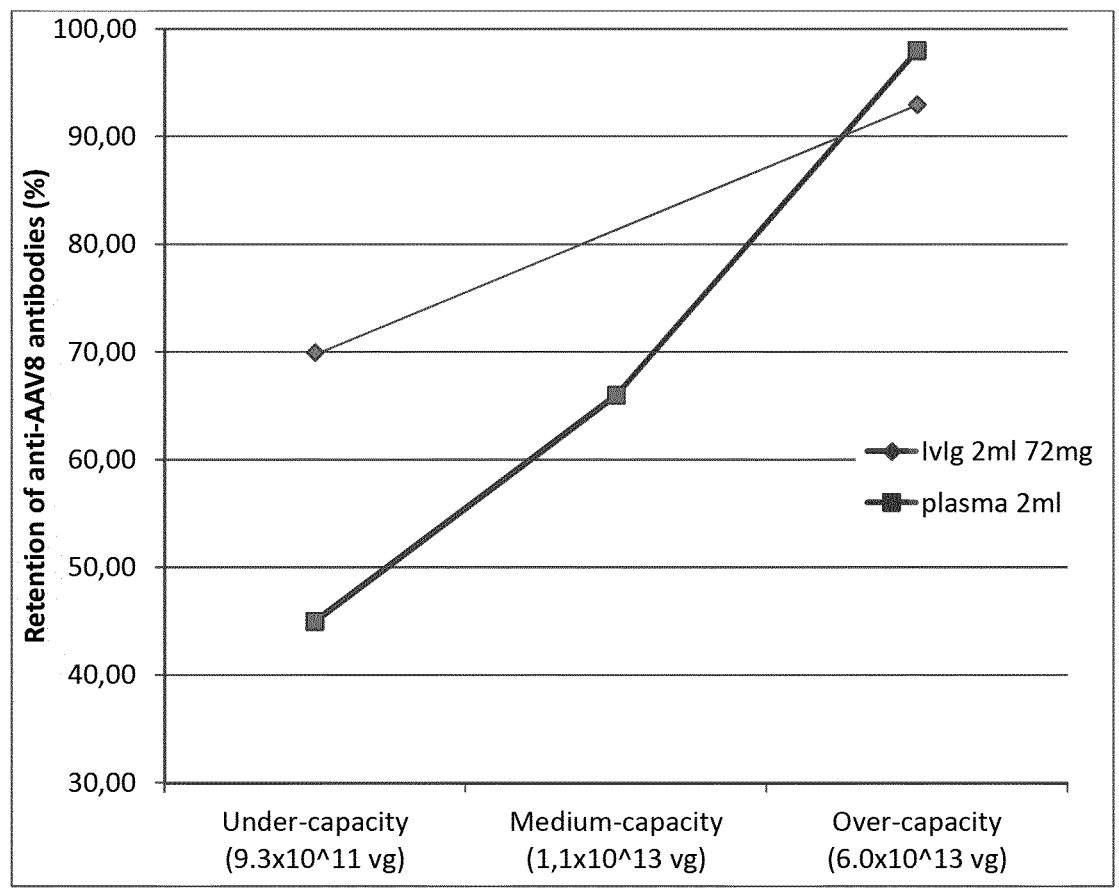

FIG. 5: Retention capacity for anti-AAV8 antibodies (contained in an IVIG composition or human plasma) is impacted by the ligand density (number of grafted AAV8 particles) per column.

Figure 6A:
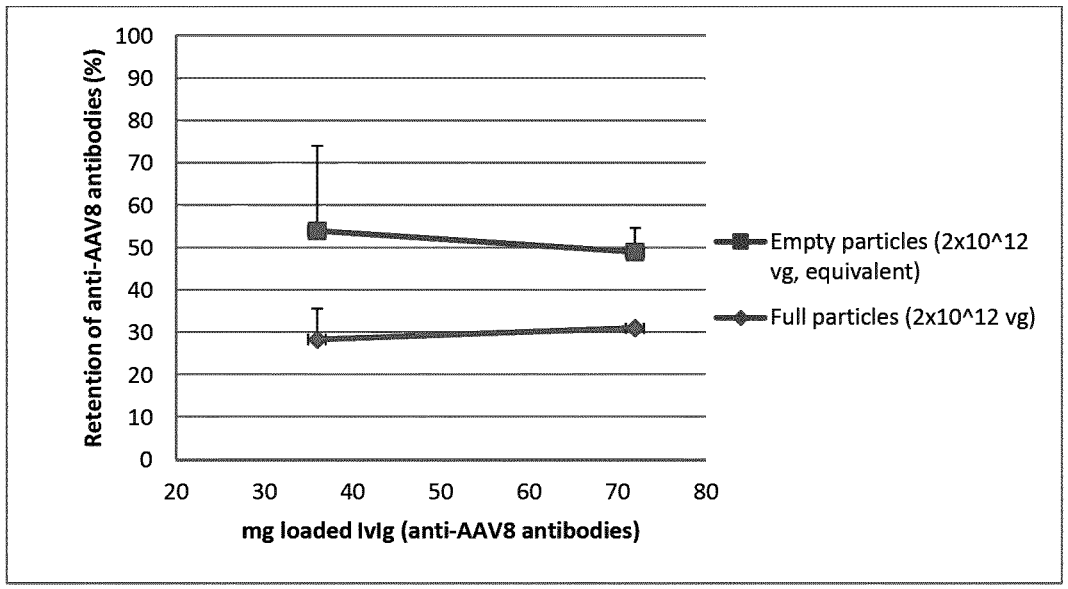

FIG. 6A. Percentage of anti-AAV8 antibody retention by affinity columns of 1ml prepared with full ($2 \times 10^{12}$ vg AAV8 grafted) or empty AAV8 particles ($2 \times 10^{12}$ vg-equivalent AAV8 grafted). Shown are the runs performed for the chromatography of 36 mg and of 72 mg of IVIG (n=2 for all conditions).

Figure 6B:
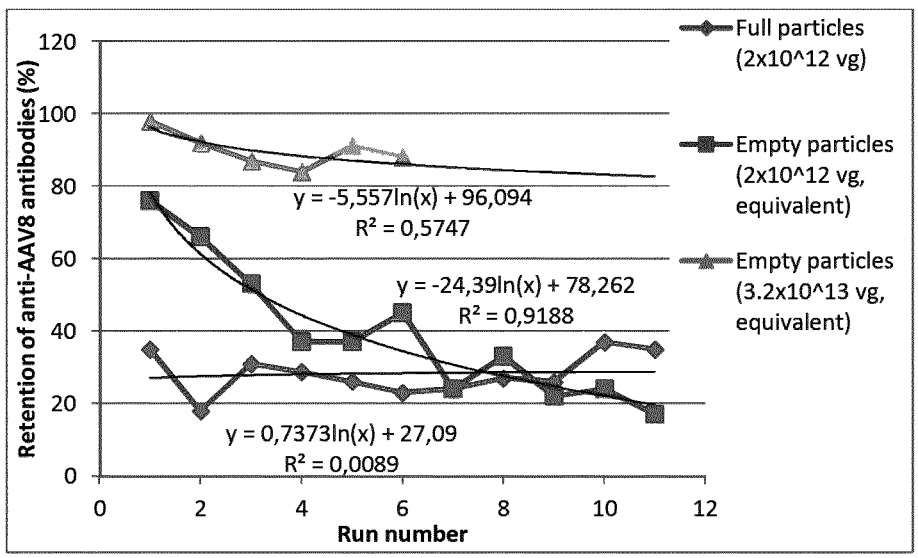

FIG. 6B. Repeated use of AAV8 columns grafted with full AAV8 particles (blue line, $2 \times 10^{12}$ vg particles) or with two different amounts of empty AAV8 particles (brown line, $2 \times 10^{12}$ vg-equivalent particles; green line, $3.2 \times 10^{12}$ vg-equivalent particles). The tests have been performed by loading 1 or 2 ml of IVIG (=36 or 72 mg) per run. The behavior of the repeated use of the AAV8 columns was modeled using logarithmic trend analysis.

Figure 7:
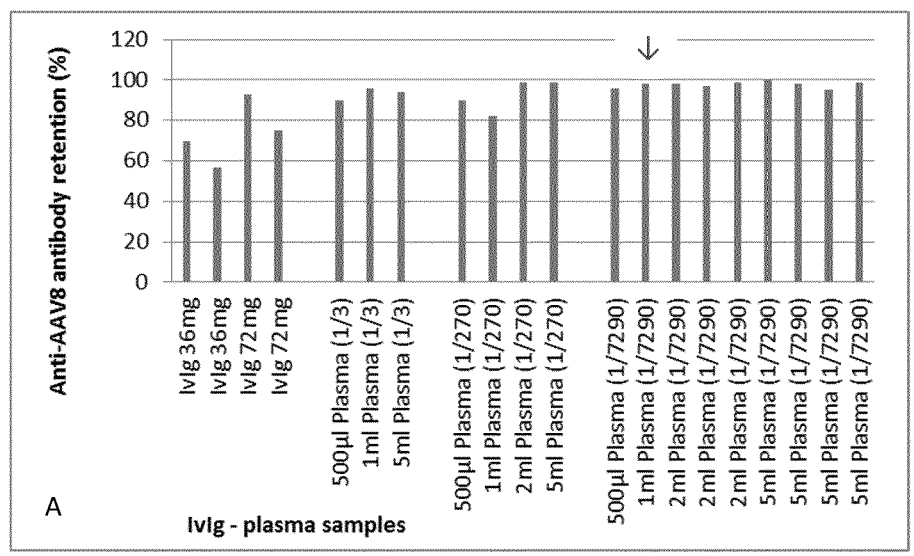
Figure 7:
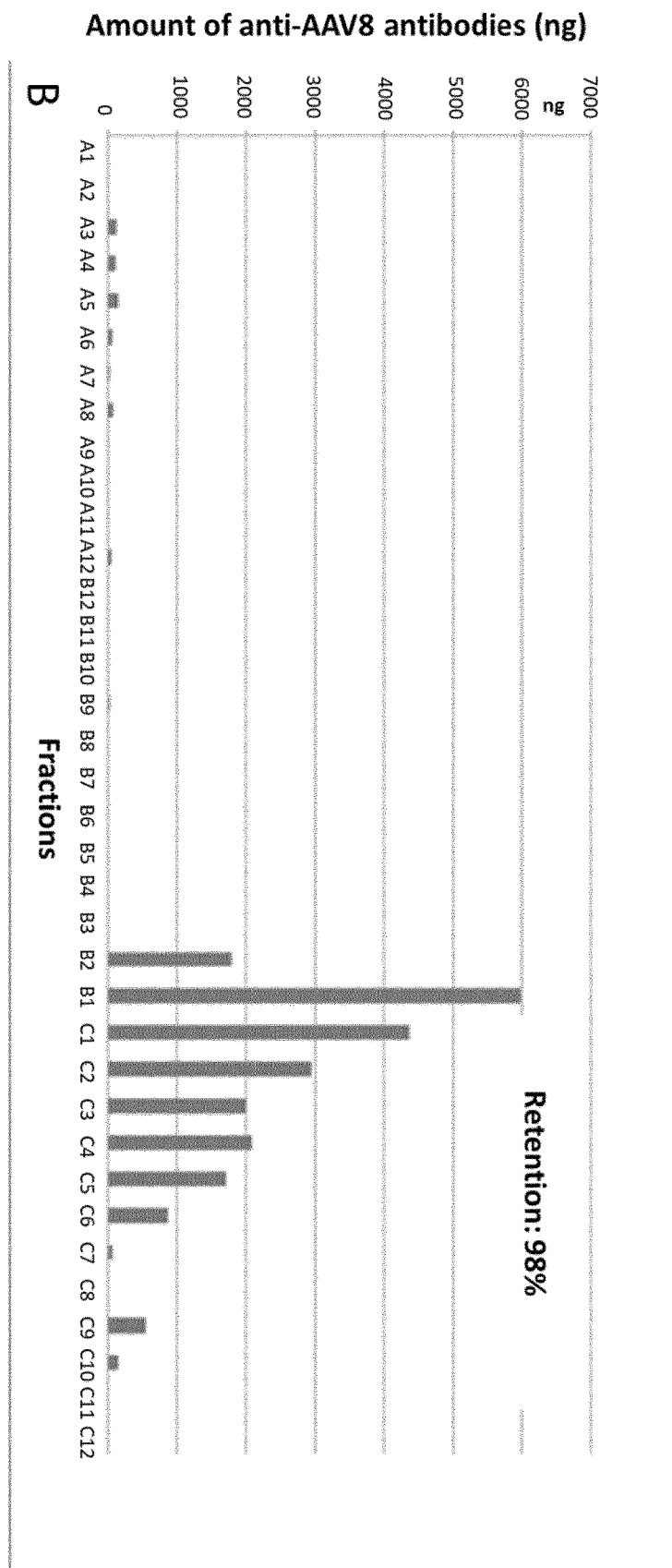

FIG. 7. A. Removal of anti-AAV8 antibodies from IVIG and plasma using a 5 ml AAV8-NHS-sepharose column grafted with $6 \times 10^{13}$ vg AAV8. In the first 4 runs, 2 different IVIG concentrations (36 and 72 mg) were loaded to the column. In all subsequent runs, different volumes of three different human plasma samples with low (titer 1/3), medium (titer 1/270), and high (titer 1/7290) anti-AAV8 antibody titers were loaded and the retention of anti-AAV8 antibodies was evaluated by ELISA. B. The totality of the fractions of the chromatography run (13, performed with a high tittering human plasma (n° 6714 160 46 57)) marked by a red arrow was analyzed for the presence of anti-AAV8 antibodies using an AAV8 ELISA: fractions A1-B4: loading of the plasma sample was followed by washing with running buffer; fractions B2-C9: elution of anti-AAV8 antibodies with a 0.1 M citrate buffer (pH 3). This analysis clearly showed that about 98% of all anti-AAV8 antibodies had been retained by the AAV8 column and only <2% of these antibodies passed into the flow through.

Figure 8:
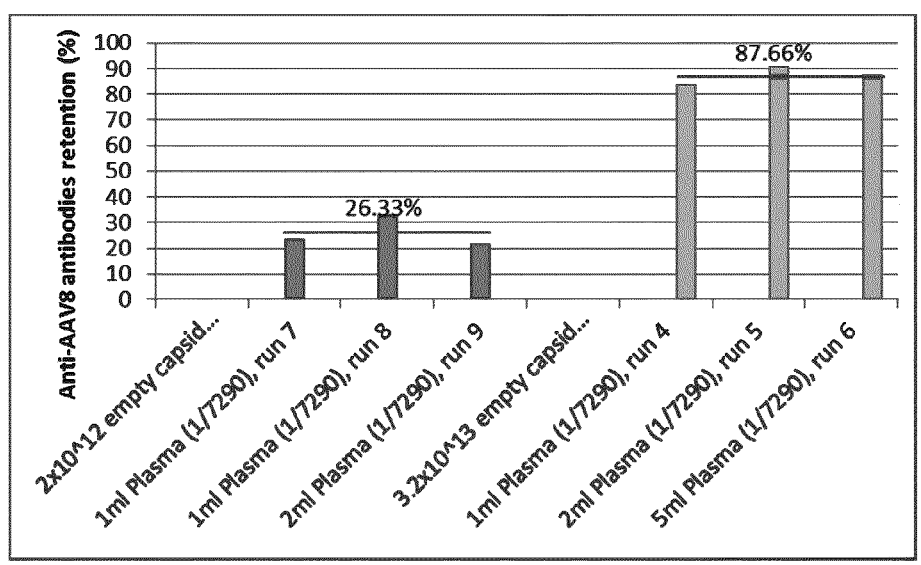

FIG. 8. Comparison of two columns grafted with a low or a high amount of empty AAV8 capsids ($2\times10^{12}$ and $3.2\times10^{13}$, respectively) for removal of anti-AAV8 antibodies from a high tittering human plasma sample (1/7290) loaded at 2-3 different volumes. The retention of anti-AAV8 antibodies was assessed by ELISA.

Figure 9:
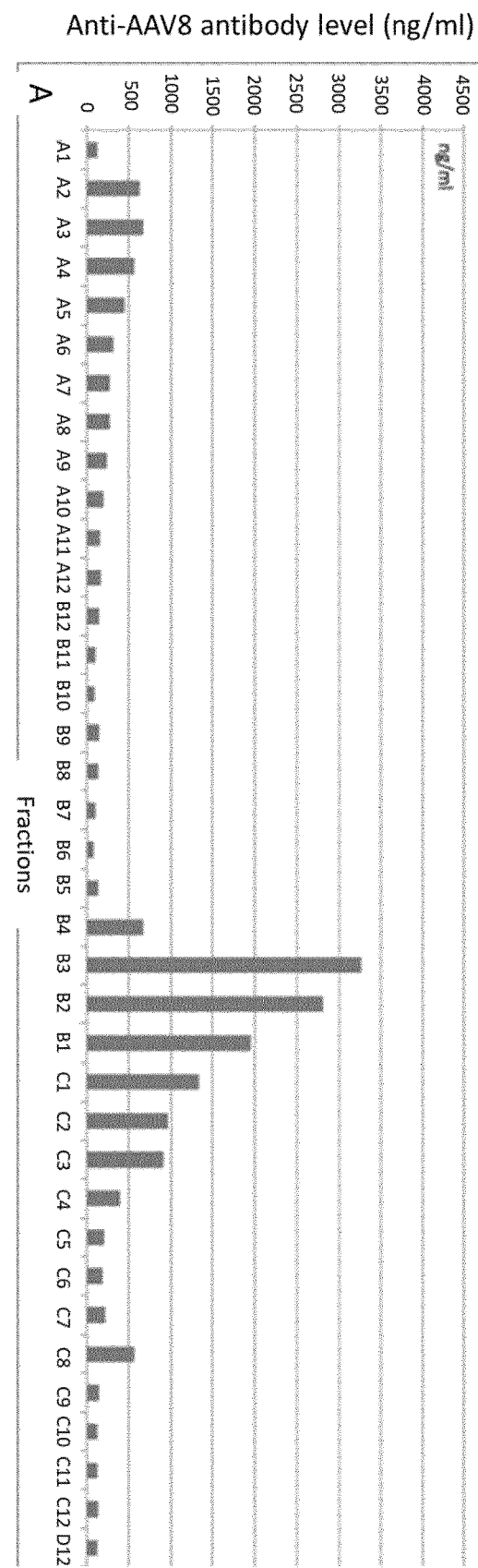
Figure 9:
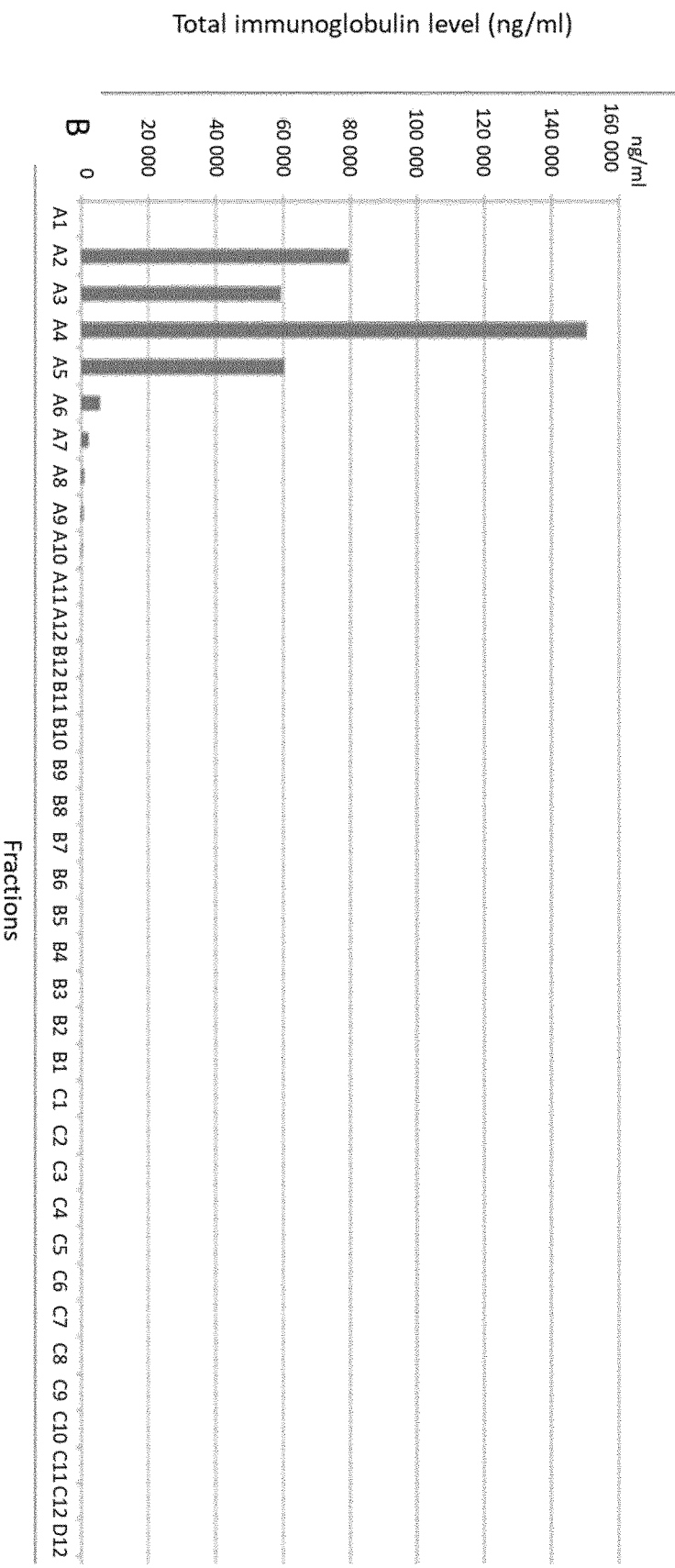

FIG. 9. Removal of anti-AAV8 antibodies (A) from the human serum sample 'DRI' by passage over an AAV8-NHS column (5 ml, grafted with $1.1\times10^{13}$vg) and evaluation of the retention/non-retention of total human immunoglobulin (B). Note: Loading and washing: fractions A1-B5; elution with citrate buffer: B4-C5.

Figure 10:
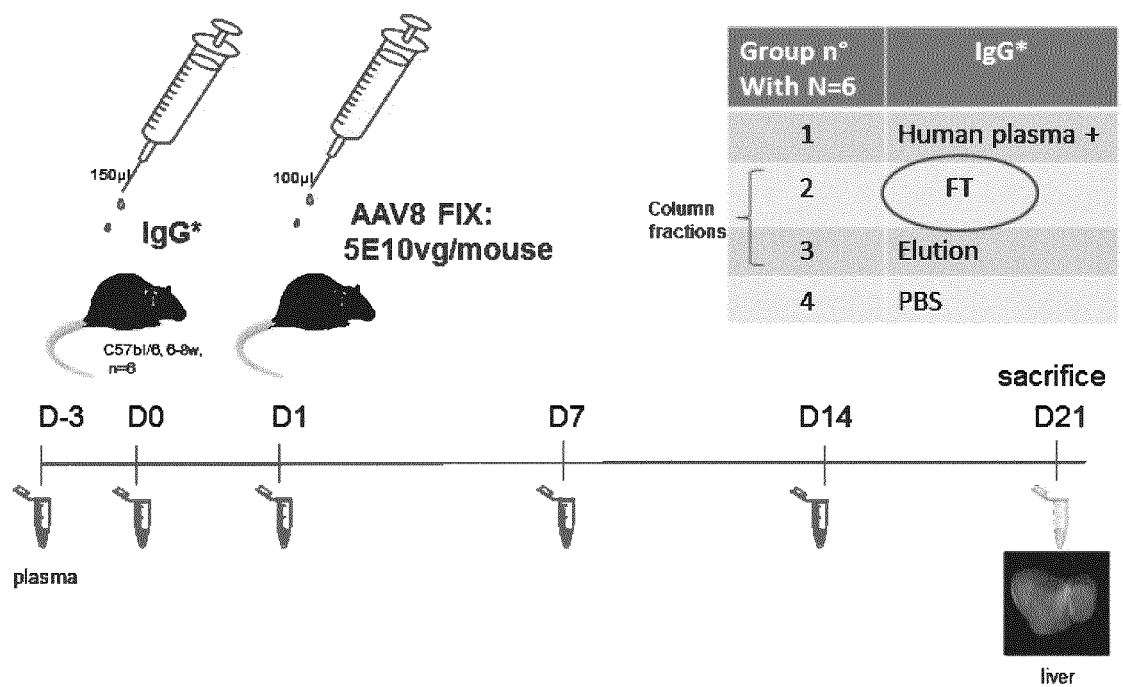

FIG. 10. Serum samples were collected 7, 14, and 21 days post-administration of AAV8-factor IX vector and at the last day, the mice were sacrificed for removal of their liver for assessing the copy number of the factor IX gene.

Figure 11:
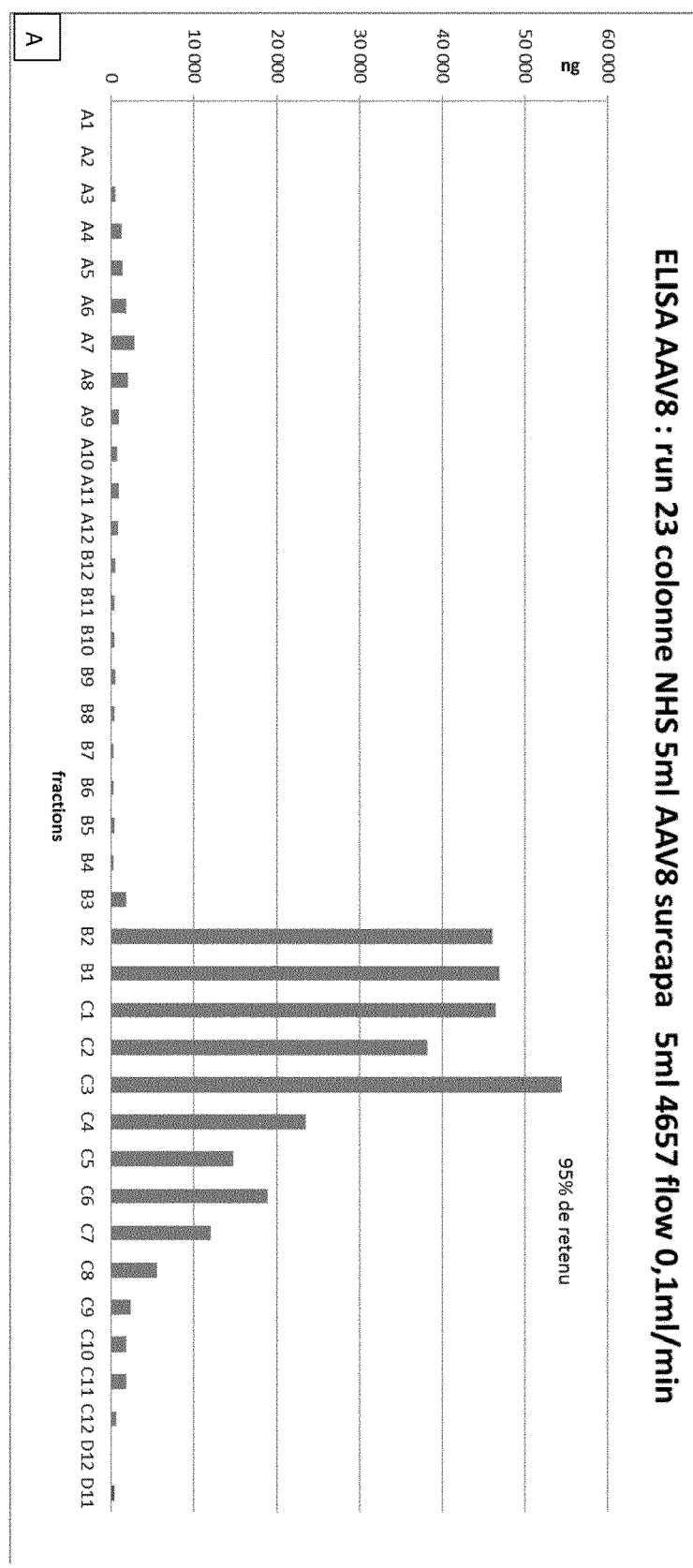
Figure 11:
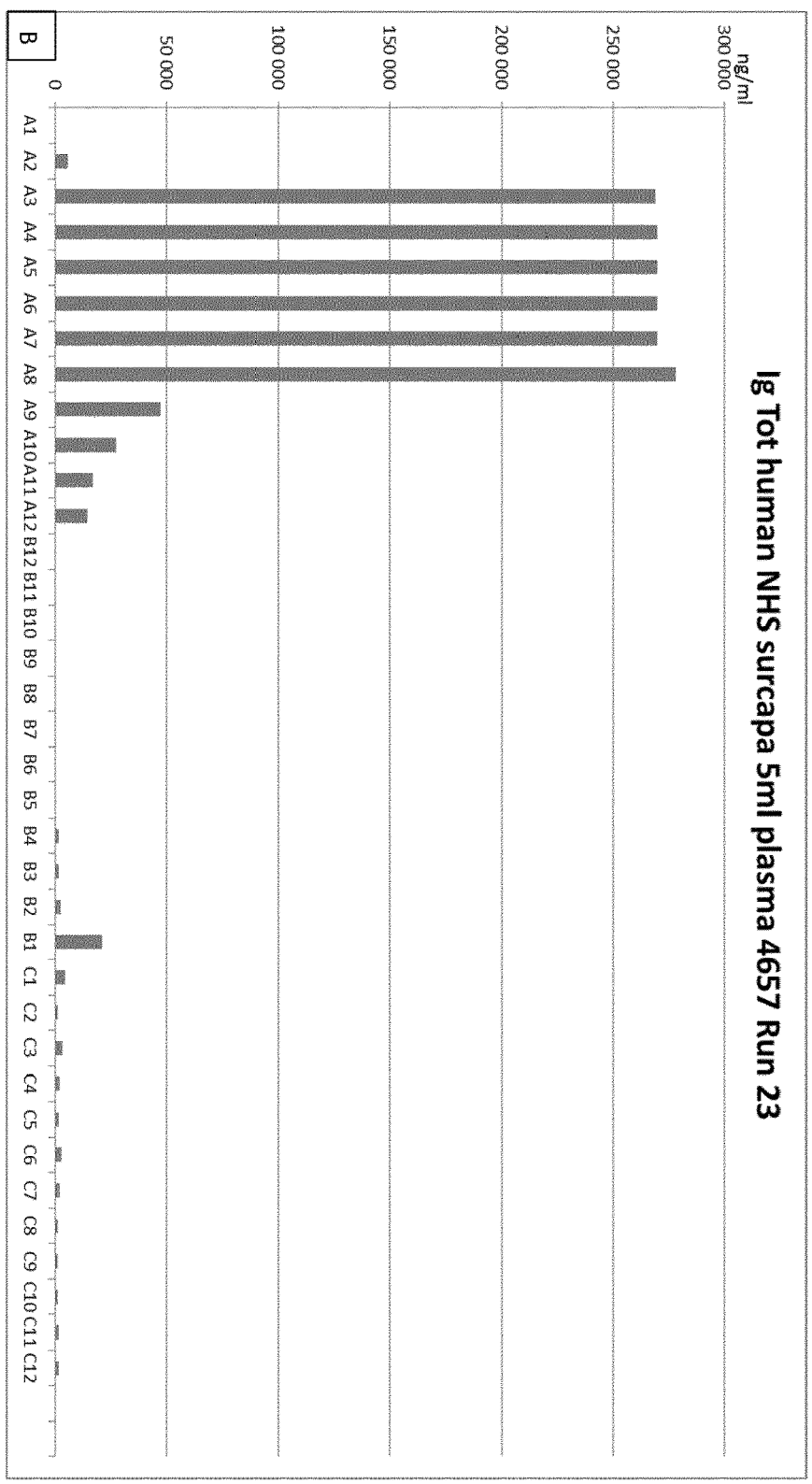

FIG. 11. Removal of anti-AAV8 antibodies (A) from the human serum sample '4657' by passage over an AAV8-NHS column (5 ml, grafted with $6\times10^{13}$ vg) and evaluation of the retention/non-retention of total human immunoglobulin (B). Note: Loading and washing: fractions A1-B5; elution with citrate buffer: B4-C5.

DETAILED DESCRIPTION OF THE INVENTION

The present invention relates to a method for removing anti-AAV antibodies, preferably anti-AAV neutralizing antibodies (NAbs), from a blood-derived composition, comprising contacting said blood-derived composition with at least one support on which one or more affinity ligand(s) specific of anti-AAV antibodies is bound.

In the context of the present invention, the terms "affinity ligand specific of an AAV serotype" and "affinity ligand that specifically binds to anti-AAV antibodies directed toward an AAV serotype" are used interchangeably.

The anti-AAV-depleted compositions obtained according to the method of the present invention possess markedly reduced anti-AAV Ab titers, especially NAb titers. These low levels of anti-AAV NAbs allow for improved AAV-based gene therapy. Indeed, blood-derived compositions treated according to the method of the present invention have advantages in the field of AAV-mediated gene therapy. Administration of the resulting purified blood-derived compositions allow the further systemic administration of AAV vectors for gene therapy without having to resort to conventional plasmapheresis, which results in total removal of circulating immunoglobulins leading to immunodeficiency requiring supplementation with purified intravenous immunoglobulins (IVIG). In addition, the present invention may be implemented on a blood-derived composition such as an IVIG preparation that may contain anti-AAV antibodies therein, thereby preventing the reintroduction of further anti-AAV antibodies to a patient in need of an AAV-based gene therapy.

The method of the present invention can be used on any blood-derived composition known to contain, or suspected of containing, antibodies against one or more AAV serotype(s). As used herein, the terms "blood-derived compositions" and "blood compositions" are used interchangeably and are meant to include whole blood, blood plasma, blood plasma fractions, blood plasma precipitate (e.g., cryo-precipitate, ethanol precipitate or polyethylene glycol precipitate), blood plasma supernatant (e.g., cryo-supernatant, ethanol supernatant or polyethylene glycol supernatant), solvent/detergent (SD) plasma, platelets, intravenous immunoglobulin (IVIG), IgM, purified immunoglobulins, or various other compositions which are derived from human or animal.

AAV is a small, nonenveloped virus of the parvovirus family that packages a single-stranded linear DNA genome, approximately 5 kb long. AAV vectors are increasingly used for in vivo gene therapy thanks to their wide range of host cells, including non-dividing cells, and to the fact that AAVs have not been associated with any human or animal disease. However, as mentioned above, anti-AAV neutralizing antibodies are highly prevalent in humans, and the frequency of subjects with detectable titers can reach up to two thirds of the population. The present invention aims at removing anti-AAV antibodies from a blood-derived composition, in order to improve AAV-mediated therapy. Anti-AAV antibodies that can be removed include antibodies to any AAV vector that could be used in AAV-mediated therapy, such as antibodies to any naturally or non-naturally occurring AAV serotype. A "serotype" is traditionally defined on the basis of a lack of cross-reactivity between antibodies to one virus as compared to another virus. Such cross-reactivity differences are usually due to differences in capsid protein sequences/antigenic determinants (e.g., due to VP1, VP2, and/or VP3 sequence differences of AAV serotypes). Under the traditional definition, a serotype means that the virus of interest has been tested against serum specific for all existing and characterized serotypes for neutralizing activity and no antibodies have been found that neutralize the virus of interest. By way of example, AAV includes various naturally and non-naturally (e.g. hybrid, chimera or shuffled serotypes) occurring serotypes. Such non-limiting serotypes include AAV-1, -2, -3, -4, -5, -6, -7, -8, -9, -10 (such as -cy10 or -rh10), -11, -rh74 or engineered AAV capsid variants such as AAV-2i8, AAV2G9, -LK3, -DJ, and -Anc80. Specific variants wherein a new glycan binding site is introduced into the AAV capsid are in particular described in WO2014144229 (disclosing in particular the AAV2G9 serotype). Other AAV serotypes include those disclosed in EP2292779, EP1310571 and U.S. Pat. No. 7,906,111. In addition, other AAV serotypes include those obtained by shuffling, as described in Koerber et al. (Molecular Therapy (2008), 16(10), 1703-1709), peptide insertion (e.g. Deverman et al., Nat Biotechnol (2016), 34(2), 204-209), or rational capsid design (reviewed in Büning et al., Curr Opin Pharmacol (2015), 24, 94-104). For the sake of convenience serotypes include AAV with capsid sequence modifications that have not been fully characterized as being a distinct serotype, and may in fact actually constitute a subgroup or variant of a known serotype.

According to the invention, a support is used onto which an affinity ligand specific of an anti-AAV antibody is bound (or "grafted", as used interchangeably herein with "bound", "bind" and declinations thereof when referring to the binding of a ligand to a support). These ligands may be any ligand that is either specifically recognized and bound by the anti-AAV antibody, or that may specifically recognize or bind the anti-AAV antibody. The term "specifically" used with respect to an affinity ligand denotes the ability of said affinity ligand to recognize a motif, sequence, or structure of its binding partner and to interact with said binding partner by spatial complementarity. An affinity ligand according to the invention "preferentially binds" to its target, meaning that it binds with greater affinity, avidity, more readily, and/or with greater duration than it binds to other substances. For example, an affinity ligand that preferentially binds to an anti-AAV8 antibody is an affinity ligand that binds this antibody with greater affinity, avidity, more readily, and/or with greater duration than it binds to antibodies different from an anti-AAV8 antibody. It should be understood by reading this definition that, for example, an affinity ligand that specifically or preferentially binds to a first target may or may not preferentially bind to a second target. As such, "preferential binding" does not necessarily require (although it can include) exclusive binding. The affinity ligand may be, for example, an antigen recognized by the anti-AAV antibody. Illustrative antigens that may be implemented in the present invention include AAV particles (e.g. genome-containing or empty AAV particles), AAV capsid proteins or fragments thereof comprising an epitope recognized by an anti-AAV antibody (such as peptide fragments of AAV capsid proteins exposed at the surface of the AAV particle), or peptides mimics of the epitope recognized by the anti-AAV antibody intended to be removed. The affinity ligand may also be selected from molecules that specifically recognize the anti-AAV antibody such as aptamers derived against an anti-AAV antibody or immunoglobulins that are produced for specifically recognizing an anti-AAV antibody.

According to the present invention, an "AAV particle" which is bound on a support is either a genome-containing AAV particle (or "genome-containing AAV capsid" or "full AAV particle" or "full particle") or an empty AAV particle (otherwise referred to as an "empty AAV capsid" or "empty AAV particle"). In a particular embodiment, the affinity ligand is a genome-containing AAV particle, an empty AAV particle, or a combination of both a genome-containing AAV particle and an empty AAV particle. In a particular embodiment, the affinity ligand is an empty AAV particle. In a particular embodiment, the affinity ligand comprises a combination of empty and full particles, with an empty:full particle ratio comprised between 1:100 and 100:1, in particular between 1:10 and 10:1, in particular between 1:5 and 5:1, in particular between 1:3 and 3:1, such as a 1:1 ratio. In a preferred embodiment, the AAV particle bound to a support is an empty or non-infectious AAV particle, which is advantageous in term of safety and with respect to the possible increased antibody binding capacity. For example, in a particular embodiment, the non-infectious AAV particle is an AAV particle (either full or empty) which lacks the vp1 protein, such as a capsid comprising only vp2 and/or vp3 capsid proteins, in particular an AAV particle whose capsid comprises only the vp3 capsid protein. In a variant of this embodiment, the AAV particle is an AAV2-derived particle. In a preferred embodiment, the AAV particle capsid comprises all AAV vp capsid proteins, i.e. AAV vp1, vp2 and vp3 capsid proteins. In a particularly preferred embodiment, the AAV particle is an empty AAV capsid, preferably an empty AAV capsid comprising all AAV vp capsid proteins, i.e. AAV vp1, vp2 and vp3 capsid proteins. AAV particles such as empty AAV particles or genome containing AAV particles, including AAV1, AAV2, AAV3, AAV4, AAV5, AAV6, AAV7, AAV8, AAV9, AAV10, AAV11, Rh10, Rh74, AAV-2i8, AAV2G9, -LK3, -DJ, and Anc80, can be constructed using recombinant techniques that are known to the skilled artisan. Full AAV particles (particles containing a vector genome) can be produced by different means by a person skilled in the art. An illustrative method of production is detailed hereinafter. Full AAV particles can be produced by transfection of, for instance, but not exclusively, HEK293 or HEK293T cells using a bi- or tri-plasmid transfection approach, in which the plasmids provide AAV helper functions (rep, cap), helper virus helper functions (in most of the cases of adenovirus 5, but not only) as well as a recombinant rAAV vector construct. 48-72 h post-transfection, AAV particles may be harvested via cell lysis. More advanced production methods include the use of stable cell lines, mainly based on HeLa cells, which contain the rep/cap functions of AAV as well as the recombinant rAAV vector construct. For producing a rAAV vector, the cells are infected with adenovirus 5 (or another virus providing helper virus function) and 72 h post-infection, AAV particles may be harvested via cell lysis. Finally, there are two further virus based production systems, the herpes simplex virus/BHK system and the baculovirus/insect cell system. The most recent versions of both systems are based on co-infection of the cells with two different viruses, one providing AAV helper functions rep and cap and the second one the recombinant rAAV vector construct. In both systems, the helper virus functions are provided by the herpes simplex virus and the baculovirus, respectively. AAV vector particles are harvested via cell lysis. For more ample information on AAV production methods, the reviews by Merten et al. (Gene Ther 2005, 12 Suppl 1, S51-61; Pharma. Bioproc. 2014, 2(2):183-203 and 2(3), 237-251) are recommended. The production of empty AAV vector particles is often an undesired by-product of the production of all AAV vector production technologies and can be separated from full AAV particles by ultracentrifugation. In this context, a specific small scale AAV vector production protocol based on precipitation and two ultracentrifugation in a CsCl gradient was reported by Ayuso et al. (Gene Ther. 2010, 17(4), 503-510) which allows the selective separation of full from empty particles. In the case that the production of empty particles only is desired, all existing production methods allow this via the omission of the recombinant rAAV vector construct during production and very high particle titers can be achieved.

In a particular embodiment of the invention, the affinity ligand which is bound to the support is an antigenic affinity ligand (for example an AAV particle (either full or empty as defined above) an AAV capsid protein or fragments thereof, or capsid peptide mimics) from a serotype that reacts with antibodies present in the subject to be treated with AAV-based gene therapy. In another embodiment of the invention, the antigenic affinity ligand bound to the support is from a serotype corresponding to the serotype of the AAV vector that will be used as a gene therapy vector in the subject to be treated, independently of whether antibodies to this serotype were detected in said subject beforehand. In another embodiment, the antigenic affinity ligand bound on the support is from a serotype different to that of the AAV vector that will be used as gene therapy vector, but is a serotype that cross-reacts with said serotype of the AAV vector that will be used as gene therapy vector. For example, AAV2 particles or AAV2 capsid proteins may be bound to the support for the purpose of removing anti-AAV8 antibodies from a blood-derived composition, due to cross-reactivity of anti-AAV8 antibodies with AAV2. Other cross-reactivities were described and are known to the prior art, such as from Boutin et al., Hum Gene Ther 2010, June; 21(6):704-12; Calcedo et al., J Infect Dis. 2009, Feb. 1; 199(3):381-90; Gao et al., J Virol 2004, June; 78(12):6381-8; and EP1310571.

In a particular embodiment, the antigenic affinity ligands specific of one or more serotype(s) are bound to the at least one support used in the method of the present invention. For example, AAV particles (either full or empty) or AAV capsid proteins (or fragments thereof), or capsid peptide mimics of more than one serotype may be bound on the same support, therefore providing a "set of antigenic affinity ligand" (e.g. a "set of AAV particles", or a "set of AAV capsid proteins", or a "set of capsid peptide mimics") onto said support. In another example, more than one support is used in the practice of the present invention, where each support may comprise bound thereon antigenic affinity ligands of only one serotype, or may comprise bound thereon a set of affinity ligands, for example a set of AAV particles (either full or empty) of different serotypes, or a set of AAV capsid proteins (or fragments thereof) of different serotypes, or a set of capsid peptide mimic of different serotypes. Any combination of serotypes can be envisioned. For example, the method of the invention may implement antigenic affinity ligands derived from any combination of the specific serotypes AAV1, AAV2, AAV3, AAV4, AAV5, AAV6, AAV7, AAV8, AAV9, AAV10, AAV11, Rh10, Rh74, AAV-2i8, AAV2G9, -LK3, -DJ, and Anc80. In a particular embodiment, a first antigenic affinity ligand specific of the AAV2 serotype is combined to any other serotype, such as any of the serotypes listed in the preceding sentence. In a particular embodiment of the invention, a set of AAV2 and AAV8 particles, or a set of AAV2 and AAV8 capsid proteins is bound on the same support. In another particular embodiment, the at least one support comprises one support on which is bound AAV2 particles or AAV2 capsid proteins, and another support on which is bound AAV8 particles or AAV8 capsid proteins.

In an alternative aspect, the support may be a molecularly imprinted polymer having affinity to one or more anti-AAV antibody.

The support of the invention may correspond to any kind of support onto which an affinity ligand can be bound, either covalently or non-covalently. The support may correspond to any type of support as above, such as a compressible (such as a compressible smooth gel, e.g. sepharose) or noncompressible support (such as a robust incompressible high porosity support), in particular a sepharose, sephadex, agarose, cellulose, modified cellulose, CPG, poros or monolith support. In a further particular embodiment, the support is a sepharose support. The attachment need not be covalent, but is at least of sufficient permanence to withstand any separation techniques (including washes and elution) that may be part of the method of the present invention. In a preferred embodiment, attachment to the support is via a covalent bond. In a particular embodiment, the affinity ligand is covalently linked to the support. In a further particular embodiment, the affinity ligand which is covalently linked to the support is an antigenic affinity ligand, such as an AAV particle (either full or empty), an AAV capsid protein (or fragment thereof), or a capsid peptide mimic. In a further particular embodiment, the antigenic affinity ligand covalently bound to the support is an AAV particle (either full or empty), such as an AAV particle selected in the groups consisting of AAV1, AAV2, AAV3, AAV4, AAV5, AAV6, AAV7, AAV8, AAV9, AAV10, AAV11, Rh10, Rh74, AAV-2i8, AAV2G9, -LK3, -DJ, and Anc80. The support may be, for example, a chomatographic column, particles or beads, Monoliths, a membrane or a filter. The support may further be a hollow fiber cartridge. The support may be an activated support, comprising functional groups allowing covalent chemical conjugation of the affinity ligand. Such activated supports include, without limitation cyanogen bromide (CNBr)-activated supports, N-hydroxysuccinimide-activated supports, carbonyl diimidazole (CDI)-activated supports, and the like. Commercially available coupling materials that may be used as described herein include, for example, CNBr Sepharose Fast Flow, NHS Sepharose Fast Flow, Epoxy Sepharose 6B, Thiol Sepharose Fast Flow, EAH Sepharose Fast Flow, Epoxy Poros EP, Aldehyde Poros AL, Epoxy Poros EP, Hydroxylated Poros OH and CDI and epoxy Monolithic materials. In a particular embodiment, the support is a NHS Sepharose support. Coupling onto such supports is well known in the art, and is typically done following the manufacturer's instructions. In addition, depending on the support chemistry and/or its coupling chemistry, a protein cross-linking compound such as formaldehyde may be used. Such a cross-linking compound may in particular be implemented on supports that activated with more labile functional groups. Accordingly, in a particular embodiment, the support functional groups are epoxy groups, and formaldehyde is used to cross-link the AAV particles or the AAV capsid proteins used in the practice of the present invention. In a particular embodiment, native, non-cross-linked AAV particles or AAV capsid proteins are implemented in the present invention. In another embodiment, an antibody specific of an AAV serotype is coupled to the support, then a preparation of the corresponding AAV serotype particle is provided, wherein the AAV particle binds to the antibody. Thereafter, covalent linking between the antibody bound to the support and the AAV particle is implemented to obtain a support able to remove anti-AAV antibodies from a blood-derived composition.

In a particular embodiment, the N-hydroxy succinimide (NHS) chemistry is implemented for covalently linking the affinity ligand.

In particular, the support is a support suitable for clinical use, i.e. a support complying with regulatory safety provisions for devices to be used in purification/preparation process of biopharmaceuticals for animal and human use.

According to the present invention, the affinity ligand density (e.g. AAV particle density or AAV capsid protein density, or capsid peptide mimic density) on the support may vary to a large extent. For example, for a volume of NHS Sepharose support of 5 mL, from $9 \times 10^{11}$ vg to $9 \times 10^{13}$ vg AAV particles may be grafted, such as $1 \times 10^{13}$ vg, $2 \times 10^{13}$ vg, $3 \times 10^{13}$ vg, $4 \times 10^{13}$ vg, $5 \times 10^{13}$ vg, $6 \times 10^{13}$ vg, $7 \times 10^{13}$ vg, $8 \times 10^{13}$ vg AAV particles. In particular, for a volume of NHS Sepharose support of 5 mL, from $5 \times 10^{13}$ vg to $7 \times 10^{13}$ vg AAV particles may be grafted, such as $6 \times 10^{13}$ vg AAV particles. Of note, the inventors observed a clear tendency that an increase in the amount of grafted AAV particles conduct to an increase in the column capacity per ml of support to that the values provided herein are only illustrative.

In another particular embodiment, the flow rate of used for conducting the present method is of between 0.01 and 1 ml/min, such as between 0.05 and 0.7 ml/min, for example between 0.1 and 0.5 ml/min (or 0.02 and 0.1 CV/min, wherein "CV" stands for "column volume"). In a particular embodiment, the flow rate is of about 0.1 ml/min (or 0.02 CV/min).

According to another aspect, the present invention relates to a support onto which an affinity ligand specific of anti-AAV antibodies is grafted, such as an antigenic affinity ligand like AAV particles (such as full or empty particles), AAV capsid proteins or fragments thereof, or capsid peptide mimics. The support may correspond to any type of support as described above, such as a compressible or noncompressible support, in particular a sepharose, sephadex, agarose, cellulose, modified cellulose, CPG, poros or monolith support. In a further particular embodiment, the support is a sepharose support. In a more particular embodiment, the support is grafted via a NHS functional group. In a further particular embodiment, the support is grafted with an antigenic affinity ligand AAV particles or AAV capsid proteins of the any serotype, such as any naturally or non-naturally occurring (such as hybrid, chimeric, shuffled serotypes) serotype, for example with an AAV1, AAV2, AAV3, AAV4, AAV5, AAV6, AAV7, AAV8, AAV9, AAV10, AAV11, Rh10, Rh74, AAV-2i8, AAV2G9, -LK3, -DJ and Anc80. In another particular embodiment, the support is grafted with AAV8 particles or AAV8 capsid proteins, or with AAV2 particles or AAV2 capsid proteins. In yet another embodiment, the support is grafted with AAV2 and AAV8 particles, or with AAV2 and AAV8 capsid proteins.

The invention also relates to an extracorporeal device through which a patient's blood or plasma can be circulated prior to being returned to the patient, said device comprising a support according to the invention. In the device of the invention, binding of the anti-AAV antibodies to the affinity ligand(s) that specifically bind to anti-AAV antibodies removes the anti-AAV antibody molecules from the patient's blood or plasma, thereby allowing further treatment of the patient with AAV-based gene therapy.

Thanks to the present invention, anti-AAV antibodies, such as anti-AAV NAbs are removed or depleted from a blood-derived composition. According to the invention, total depletion of anti-AAV antibodies, in particular NAbs, is not required, as long as the reduction in antibody titers allows an improvement in AAV vector transduction when AAV-based gene therapy is carried out after implementation of the above method. For example, antibody titer reduction may be of at least 1 log, 2 logs, 3 log, or at least 4 logs. For example, with the described method, an anti-AAV neutralizing antibody titer of 1:3,160 can be reduced to 1:1 (negative titer).

According to a particular embodiment, the blood-derived composition is passed once or several times through the at least one support described above. In a further particular embodiment, in case of implementation of multiple supports, such as supports each containing affinity ligand specific of different AAV serotypes, the support may be serially arranged.

In another embodiment, the same column is used for more than one retention cycle (either for the same blood-derived composition, or different compositions, preferably for the same).

Accordingly, another aspect of the invention relates to a composition obtainable by applying the method described above on a blood-derived composition. The composition of the invention is therefore a blood-derived composition with reduced amounts (or titers) in AAV antibodies. In a particular embodiment, the anti-AAV antibody presence or content in the blood-derived composition is determined before applying the method of the present invention. In another embodiment, the presence or content of anti-AAV antibodies is not determined before application of the method of the present invention. In a particular embodiment, the composition of the present invention is obtainable from a blood-derived composition that contains anti-AAV antibodies. The resulting composition is thus a composition with reduced amounts (or titers) of anti-AAV antibodies as compared to the blood-derived composition before application of the method of the invention. As mentioned, the blood-derived composition may in particular be whole blood, blood plasma, blood plasma fractions, blood plasma precipitate (e.g., cryoprecipitate, ethanol precipitate or polyethylene glycol precipitate), blood plasma supernatant (e.g., cryosupernatant, ethanol supernatant or polyethylene glycol supernatant), solvent/detergent (SD) plasma, platelets, intravenous immunoglobulin (IVIG), IgM, purified coagulation factor concentrate, fibrinogen concentrate, or various other compositions which are derived from human or animal. In a particular embodiment, the blood-derived composition is whole blood or an IVIG composition.

The present invention also provides a method for improving transduction efficiency of an AAV gene therapy vector. A number of embodiments are envisioned in this regard and are encompassed by the present invention. In a first embodiment, the above method for removing anti-AAV (neutralizing) antibodies is applied to the whole blood of a subject who is a future receiver of an AAV-based gene therapy, thereby reducing anti-AAV (N)Abs titers in said whole blood. In this embodiment, the blood of the subject is moved from the subject along a pathway comprising the at least one support described above, and the anti-AAV (N)Ab-depleted blood is returned to the subject's internal circulation. In a second embodiment, the subject's blood may be subjected to classical plasmapheresis, thereby non-specifically removing all or almost all antibodies from said blood, including anti-AAV (N)Abs. In this second embodiment, an IVIG composition is submitted to the method for removing anti-AAV (N)Abs according to the invention, and this processed IVIG composition is then administered to the subject who was previously subjected to plasmapheresis, thereby preventing the IVIG composition from reintroducing anti-AAV (N)Abs into the subject's circulation. In a particular embodiment, the subject's blood is subjected to one or more cycles of anti-AAV antibody depletion according to the present invention, such as to 1, 2, 3, 4, 5, 6, 7, 8, 9, 10, 11 or 12 cycles of anti-AAV antibody depletion (be it according to the method of the present invention, using one or more supports grafted with one or more affinity ligands as defined above, or using classical plasmapheresis followed by the injection of an anti-AAV-depleted IVIG composition).

The subject treated as provided in the preceding paragraph is then administered with the AAV gene therapy vector, comprising a therapeutic gene of interest selected for treating the subject's condition. Ideally, the AAV gene therapy vector is administered as soon as possible after the subject has been treated as provided above. In particular, the subject is treated before anti-AAV titers raise again. In a particular embodiment, to optimize gene therapy efficiency, the subject treated as provided in the preceding paragraph is administered with an immunosuppressive compound before administration of the AAV gene therapy vector. Illustrative immunosuppressive compounds include, without limitation, rituximab, ocrelizumab, bortezomib, ibrutinib, ciclosporin A, calcineurin inhibitors, rapamycin, corticosteroids, mycophenolate mofetil, atacicept, baff inhibitors, BLyS and APRIL inhibitors.

The present invention thus also relates to an AAV vector for use in a method for the treatment of a disease by gene therapy, wherein the AAV vector comprises a therapeutic gene of interest appropriate for the treatment of said disease, wherein said AAV vector is of a given serotype, wherein said AAV vector is for administration to a subject in need thereof, after administration to said subject of a blood-derived composition which has been processed according to the method for removing anti-AAV antibodies described above, to remove anti-AAV antibodies specific of said given serotype from said composition.

The invention also relates to a method for the treatment of disease in a subject in need thereof by gene therapy, wherein the disease is treated by administering to said subject an effective amount of an AAV vector comprising a therapeutic gene appropriate for treating said disease, wherein said AAV vector is of a given serotype, and said AAV vector is for administration to said subject, after administration to said subject of a blood-derived composition which has been processed according to the method for removing anti-AAV antibodies described above, to remove anti-AAV antibodies specific of said given serotype from said composition.

The present invention may generally be applied for therapy of any disease that may be treated by expression of a therapeutic gene in a cell or tissue of a subject mediated by an AAV vector. These include, for example, proliferative diseases (cancers, tumors, dysplasias, etc.), infectious diseases; viral diseases (induced, e.g., by the Hepatitis B or C viruses, HIV, herpes, retroviruses, etc.); genetic diseases (cystic fibrosis, dystroglycanopathies, myopathies such as Duchenne Muscular Myopathy; myotubular myopathy; hemophilias; diabetes; amyotrophic lateral sclerosis, motoneurones diseases such as spinal muscular atrophy, spinobulbar muscular atrophy, or Charcot-Marie-Tooth disease; arthritis; cardiovascular diseases (restenosis, ischemia, dyslipidemia, homozygous familial hypercholesterolemia, etc.), or neurological diseases (psychiatric diseases, neurodegenerative diseases such as Parkinson's or Alzheimer's, Huntington's disease addictions (e.g., to tobacco, alcohol, or drugs), epilepsy, Canavan's disease, adrenoleukodystrophy, etc.), eye diseases such as retinitis pigmentosa, Leber congenital amaurosis, Leber hereditary optic neuropathy, Stargardt disease; lysosomal storage diseases such as San Filippo syndrome; hyperbilirubinemia such as CN type I or II or Gilbert's syndrome, Pompe disease, etc.

The invention will now be described with reference to the following non-limiting examples.

EXAMPLES

Materials and Methods:
Vector Preparation:
Full AAV8 Vector Particles:

Sf9 cells (Gibco) were grown in suspension culture at 27° C. in SFM900III medium (Invitrogen) using 1 L Corning Erlenmeyer Flasks. The baculovirus system used was the system as published by Smith et al. (Mol. Ther., 2009, 17(11), 1888-1896). Baculoviruses were generated according to the guidelines of the Bac-to-Bac protocol and were amplified in suspension cultures of Sf9 cells in 250 mL Erlenmeyer Flasks. rAAV production were performed by dual infection of baculoviuses harboring the recombinant AAV genome (γSGC) and AAV rep/cap genes, each at an MOI of 0.05 (PFU titer) in 70 mL of Sf9 cell culture seeded at $10^6$ cells/mL in 250 mL Erlenmeyer Flasks. At 96 h post-infection, 1 mL of the total culture was recovered for direct quantification of rAAV production prior to purification.

Empty AAV8 Vector Particles:

The empty AAV8 vector particles were prepared according to Ayuso et al. Gene Therapy 2010.

Vector Titration:

rAAV Vector Genome (vg) Titration Using qPCR

A quantitative PCR assay was performed directly on the total culture samples or purified rAAV samples to determine the rAAV titer (viral genome copies per ml of culture). Viral DNA was extracted directly from the bulk or from purified samples using the MagNA Pure DNA and viral NA small volume kit (MagNA Pure 96, Roche). QPCR titrations were performed against a reference on a Roche LightCycler 480II using primers and probe ITR-F/R/P for rAAV genome titration:

```
Forward:
                                    (SEQ ID NO: 1)
5'-AAGTCGGTCCCAAAATGGTAGA-3'

Reverse:
                                    (SEQ ID NO: 2)
5'-TGCCGTCGTTGGAGTTGA-3'

Probe:
                                    (SEQ ID NO: 3)
5'-CAGAATCAACAGTTTCAG-3'
[5']6-FAM[3']MGB-NFQ probe.
```

Determination of Empty AAV Vector Titers by Sypro Ruby Staining:

Purified AAV samples were migrated on a SDS-PAGE (NuPAGE Novex 1.5 mm 4-12% gel from INVITROGEN) by loading 1-10 µl of prepared sample per lane (most commonly: 2 µl per lane).

The required volumes of samples were taken and put into an Eppendorf 1.5 mL tube. Different points of standard curve were prepared: 5 µL, 3 µL, 2 µL, 1 µL and 0.5 µL of standard (volumes can change depending of the experiments and range of expected results). Samples and standards filled up to 20 µL using water. A mix containing 7.5 µL/sample of NuPage LDS Sample buffer (4×) and 3 µL/sample of NuPage reducing agent (10×) was prepared and mixed with the samples. The total final volume of each sample was of 30.5 µL. Then the samples were denaturated during 5 min±2 min at 95° C.±2° C. followed by centrifugation for 10 sec using a bench-centrifuge.

After preparation, electrophoresis tank and mounting of the gel, 3 µL of ladder (PPP) and 30 µL of samples were loaded and run during 2 h at 120-150 Volts using MES SDS running buffer 1×. The migration was stopped and the gel was transferred in a box (which has a cover) containing a little bit of running buffer to not let dry the gel.

The running buffer contained in the box was removed and replaced by 100 mL of fixation solution (put on the gel). The cover was closed and the box was agitated during 30 min. The solution was removed and this step was repeated with 100 mL of fresh fixation solution.

The fixation solution was replaced by 60 mL of SYPRO Ruby stain protein. The box was closed and protected from the light (in alu paper) and slowly agitated overnight.

In the next morning the Sypro Ruby was removed and replaced by 100 mL of wash solution. The box was incubated and agitated during 30 min. The box was maintained protected from light. Before reading the gel in the Gbox the gel was washed 2 times in water. In the Gbox, the gel was exposed to 200 msec and a picture is taken. The Licor software "image studio lite" was used to analyze and quantify the signal of VP3 in each sample. The sample concentration/titer was expressed as capsid equivalents per ml.

Grafting of AAV Particles to Different Column Matrices:

We prepared a column to which empty or full AAV2 or AAV8 capsids were bound or covalently linked to capture anti-AAV antibodies. The idea was to use a specific column to pass the plasma once or multiple times and remove anti-AAV antibodies.

AVB sepharose (GE HealthCare)—immune-affinity based retention of AAV particles:

This concept was first proven on an AVB Sepharose gel column (llama antibodies) on which an AAV8 particles were immunologically retained. For 1 mL of AVB gel, loaded with $1.2 \times 10^{11}$ vg of AAV8 particles, anti-AAV antibodies were depleted from 0.5 mL (25 mg) of a commercial IVIG composition.

Evaluation of different chromatographic supports for the covalent coupling of AAV particles:

The purpose was also to provide supports onto which the AAV particles are covalently attached. Preliminary experiments allowed evaluating the different resins to build the column, which is the one that retains the antibodies best and allows for multiple uses. Several column materials and chemistries were tested, among which a CDI Monolith, an EPO Monolith (both from Bia Separations), an EPO POROS (from Thermo Fisher), and a NHS sepharose gel (HiTrap NHS; from GE HealthCare). After testing these various column chemistries Sepharose was retained as the most promising column material. However, other column materials provided interesting results and any other column may be adapted to the method provided herein, based on in vitro and in vivo results. Furthermore, both native AAV particles and AAV particles that were cross-linked with formaldehyde were tested in the columns (in particular the EPO POROS column) The ideal material to deplete anti-AAV antibodies resulted to be native/unmodified AAV capsids on a NHS Sepharose column, although cross-linked AAV particles proved to be of interest in certain circumstances such as with support materials comprising epoxy functional groups such as the EPO POROS column. The covalent bond with the NHS chemistry seems to be more stable than with the epoxy chemistry. We saw a leakage of AAV8 with the Epoxy support if no crosslink is applied, but with formaldehyde cross-link the AAV8 graft was more resistant and acceptable.

Data comparing results obtained with different conditions (column chemistry and optional addition of formaldehyde) are shown in the following tables:

Experimental information with respect to the EPO POROS column:

After grafting the column was further incubated with or without formaldehyde. The incubation with formaldehyde was chosen for increasing the stability of graft/reducing AAV particle leakage.

About 1 ml of chromatography support with $1.6 \times 10^{12}$ vg AAV8

Grafting: 86 h 2 h ethanolamine at room temperature for inactivating the residual active sites of the support. PBS wash or further incubation with formaldehyde (37% at 1/200 in PBS) for 15 days followed by neutralizing with sodium meta bisulfite 3.75% w/v at 1/100 in PBS 2 h TA and washing with PBS.

5 runs (flow rate: 0.5 ml/min (equivalent to 0.5 CV/min)), with a starting material consisting of 0.5 mL IVIG diluted 4 times and formulated in PBS, corresponding to 25 mg of IVIG.

Results were more homogenous when the AAV graft was stabilized by formaldehyde, than without this stabilisation:

| POROS EPO without FORMALDEHYDE | | |
|---|---|---|
| run number | total IvIg (ng/ml) | % retained |
| run 1 | 53285 | 79.54% |
| run 2 | 10884 | 11.15% |
| run 3 | 40891 | 62.21% |
| run 4 | 53116 | 68.96% |
| run 5 | 2792 | 46.13% |

| POROS EPO with FORMALDEHYDE | | |
|---|---|---|
| run number | total IvIg (ng/ml) | % retained |
| run 1 | 1301 | 8.75% |
| run 2 | 20964 | 39.62% |
| run 3 | 30838 | 51.58% |
| run 4 | 43784 | 39.97% |
| run 5 | 41582 | 50.50% |

Experimental information with respect to the NHS sepharose HiTrap column:

5 ml gel with $1.9 \times 10^{12}$ vg AAV8

Grafting: 1 h 30 min ethanolamine at room temperature

PBS wash.

Grafting was carried out more rapidly than with other columns.

5 runs (program: 0.5 ml/min (equivalent to 0.1 CV/min)), with a starting material consisting of 2 mL IVIG diluted 1.4 times with PBS, corresponding to 71 mg of IVIG

| 5 ml NHS column | | |
|---|---|---|
| run number | total IvIg (ng/ml) | % retained |
| run 1 | 10209 | 25.84% |
| run 2 | 13148 | 33.06% |
| run 3 | 14974 | 36.02% |
| run 4 | 13358 | 44.03% |
| run 5 | 16203 | 38.02% |

It is apparent that in case of the POROS column, the best results are obtained without a treatment with formaldehyde for cross-linking the AAV8 capsids. In addition, these data show that the NHS sepharose gel provides a more reliable and reproducible retention.

On the NHS Sepharose column, optimal flow rate was determined to be of 0.1 mL/min (0.02 CV/min), which was the flow rate that allowed the best anti-AAV8 antibody retention.

This column was further tested by passing an IVIG composition through the column multiple times. The anti-AAV titer was then measured. Instead of a single run we performed multiple runs on the same column to mimic the scenario in the clinic.

Conditions were as follows:

5 ml gel with $9.30 \times 10^{12}$ vg AAV8

1 ml IVIG+4 ml PBS (36 mg of IVIG)

Flow rate 0.1 ml/min

It was observed that successive passages were able to remove completely the anti-AAV antibodies from the column. This was further confirmed by eluting the content of the column at the end of the experiment, which released large quantities of IgG specific to AAV8 that were retained by the column.

Columns serially arranged were further evaluated. Retention ratio after passage through a single AAV8 column, or through serially arranged AAV8/AAV8, AAV2/AAV8 and AAV8/AAV2 columns showed a better retention than with a single column.

| IVIg (mg) | Run | % retention |
|---|---|---|
| 140 | AAV8 | 37% |
| 140 | AAV8-AAV8 | 58% |
| 140 | AAV2-AAV8 | 53% |
| 140 | AAV8-AAV2 | 53% |
| 70 | AAV8 | 58% |
| 70 | AAV8-AAV8 | 81% |
| 70 | AAV2-AAV8 | 86% |
| 70 | AAV8-AAV2 | 84% |

The % of retention was evaluated by anti-AAV8 ELISA. All the fractions were analyzed by ELISA and the % of retention was calculated as follows:

% of retention=(totally eluted antibodies/(totally eluted antibodies+antibodies presented in the flow-through)

In order to be closer to the clinical reality (plasmapheresis of patients), it was decided to perform supplementary tests using sera and plasma samples from animals (dog, macaque) and humans.

Loading of serum from man, dog and macaque to anti-AAV8 column:

Sample volume loaded per AAV8 column: 350 µL/5 ml column ($1.1 \times 10^{13}$ vg/column)

Test for anti-AAV8 antibodies in the different fractions of the affinity chromatography runs.

For the three samples, practically all anti-AAV8 antibodies have been retained.

Further experiments were conducted on human plasma samples. 1 mL and 2 mL of two different plasma samples were applied on a 5 mL AAV8 column ($1.6 \times 10^{13}$ vg grafted per column) This resulted in about 98% and 99% anti-AAV8 antibody retention, respectively. Therefore, human plasma samples with high anti-AAV8 titers were efficiently depleted for anti-AAV8 antibodies after one passage on the AAV8 particle-grafted NHS Sepharose column of the invention.

Comparison of the grafting of full or empty particles—effect of using empty particles:

Both columns were grafted with the same quantity of AAV particles ($2 \times 10^{12}$ capsids/ml). The IVIG samples were prepared as follows:

Use of PD-10 Desalting Columns GE ref 17-0851-01 by gravity protocol.

Reformulation in PBS at 36 mg/ml

Result: the column with empty capsids grafted showed considerably higher removal efficiency than the column grafted with full particles. This is valid for different ligand (AAV) densities.

The experiments have been done with two different batches of empty AAV8. All results point to the best anti-AAV8 retention when using empty AAV8 capsids.

In Vivo Experiments (Proof of Concept):

Finally, in vivo experiments were conducted for proving that the removal of anti-AAV8 antibodies from serum/plasma of dogs (as a model) renders liver gene therapy possible for anti-AAV8 positive animals (model: haemophilia B). Mice have been injected with four different samples: anti-AAV8 positive dog serum (non-treated by AAV8 affinity chromatography), flow-through of this serum passed over an anti-AAV8 column, elution peak of the retained serum-fractions and serum from a naïve dog as negative control. The injection scheme and sampling scheme is shown in FIG. 1.

The experimental plan was the following:

50 male C57bl6 mice (8 weeks of age) were treated and blood/plasma was taken at the following time points: D-3, D1, D7, D14, and D28

D0: IV injection into tail vein: 100 µl of dog Ig (Anti-AAV8 positive, column flow through, eluted fractions from the column, naive dog serum)

D1: IV injection into tail vein: 100 µl of AAV8-hFIX.

5 samplings of plasma: D-3 before injection of Ig, D1 before injection of AAV8, D7, D14, and D28 before sacrifice Methods: Anti-AAV8 IgG were Determined as Previously Described (Mingozzi et al., Gene Ther 2013)

For binding ELISA we used the protocol described in Mingozzi et al., Gene Therapy 2013.

Determination of AAV Vector Neutralizing Antibodies (NABs):

We essentially used the protocol for NAb published by Meliani et al. (2015) [Hum. Gene Ther. Methods].

Analysis of FIX Expression in Animals

Done by ELISA as described in Mingozzi et al., Science Translational Medicine 2013

Detection of Vector Genome Copy Numbers in Livers of Injected Animals.

Done by QPCR as described in Mingozzi et al., Science Translational Medicine 2013

Result: the mice injected with dog serum containing anti-AAV8 antibodies do not show liver transduction, meaning that the dog anti-AAV8 antibodies neutralized the injected AAV8. However, the removal of these anti-AAV8 antibodies using an AAV8 affinity column from the positive dog serum eliminated this neutralizing effect and the injected AAV8 efficiently transduced liver cells which became positive for the factor IX gene. The serum from a

| Col NHS 1 mL 2e12 capsids | 1 mL of IVIG (36 mg) | 1 mL of IVIG (36 mg) | 1 mL of IVIG (36 mg) | 1 mL of IVIG (36 mg) | 2 mL of IVIG (72 mg) |
|---|---|---|---|---|---|
| AAV8 empty | 76% | 66% | 37% | 37% | 53% |
| AAV8 full | 23% | 24% | 27% | 26% | 31% |

| Col NHS 5 mL 3.2e13 capsids | 1 mL of IVIG (36 mg) | 1 mL of IVIG (36 ml) | 2 mL of IVIG (72 mg) |
|---|---|---|---|
| AAV8 empty | 98% | 92% | 87% |
| AAV8 full | 70% | 57% | 75%% | naïve dog had no inhibitory effect on liver transduction. The liver cells were positive for the factor IX gene.

General Conclusion:

The immune-affinity column based on Sepharose (grafted with AAV8 using the NHS chemistry) is efficient and specific for removing anti-AAV8 antibodies either from human IVIG samples, from human and animal sera as well as from human plasma. The best ligand (AAV8 particles) density is $1.6 \times 10^{13}$ vg/column (5 ml column) and it could be shown that the use of empty particles is much more efficient for anti-AAV removal than when using full particles. Other AAV serotypes can also be coupled.

Results:

Choice of the Column Matrix:

Monolith CDI and EPO:

The initial evaluation of different column material was governed by the idea that a incompressible ('hard') and eventually scalable chromatography column should be developed allowing use in an industrial pharmaceutical environment in view of the large-scale production of IVIG devoid of anti-AAV antibodies. Therefore initially, the incompressible supports including Monolith chromatography and Poros have been evaluated.

Poros EPO with and without Crosslinking Using Formaldehyde:

Following the evaluation of the Monolith support, another incompressible chromatographic support Poros matrix was included because of its advantages with respect to the flexible choice of the working volume. In this specific case, only the EPO chemistry was available, as for the Monolith EPO support. Since we have observed that there is a certain leakage of AAV grafted via the EPO chemistry or a degradation (damaging), we have compared columns to which AAV particles have been simply grafted via the EPO chemistry with those for which the grafted AAV particles have been further crosslinked via formaldehyde.

In both cases, by always using the same 1 mL columns, to which $3.7 \times 10^{11}$ vg of AAV8 particles have been grafted, five runs with one IVIG preparation (18 mg per injection) and three different sera (DRI (human), TIM (macaque), 30551 (macaque)) (190 µl per injection) were performed. The results indicated that both columns were able to retain anti-AAV8 antibodies (Table 1).

TABLE 1

Evaluation of two AAV8 columns based on the Poros EPO support, for the removal of anti-AAV8 antibodies from different samples:

| Sample | Quantity/volume of applied sample | Total (ng) | Flow-through (ng) | Elution (ng) | Yield (%) |
|---|---|---|---|---|---|
| AAV8 grafted to column without formaldehyde treatment | | | | | |
| IvIg (1) | 18 mg | 19 255 | 1 899 | 17 356 | 90 |
| IvIg (2) | 18 mg | 22 327 | 2 643 | 19 683 | 88 |
| IvIg (3) | 18 mg | 22 314 | 2 077 | 20 236 | 91 |
| IvIg (4) | 18 mg | 17 273 | 2 628 | 14 645 | 85 |
| IvIg (5) | 18 mg | 26 780 | 2 660 | 24 121 | 90 |
| Human serum (DRI) | 190 µL | 8 505 | 8 280 | 225 | 97 |
| Macaque serum (TIM) | 190 µL | 51 572 | 20 528 | 31 044 | 60 |
| Macaque serum (30551) | 190 µL | 47 003 | 6 856 | 40 146 | 85 |
| Means ± SD | — | — | — | — | 85.75 ± 11.08 |
| AAV8 grafted to column with formaldehyde treatment | | | | | |
| IvIg (1) | 18 mg | 9 292 | 1 899 | 7 393 | 80 |
| IvIg (2) | 18 mg | 9 348 | 1 716 | 7 632 | 81 |
| IvIg (3) | 18 mg | 41 213 | 9 656 | 31 557 | 77 |
| IvIg (4) | 18 mg | 45 142 | 7 720 | 37 422 | 83 |
| IvIg (5) | 18 mg | 36 320 | 4 904 | 31 417 | 86 |
| Human serum (DRI) | 190 µL | 25 981 | 3 866 | 22 115 | 85 |
| Macaque serum (TIM) | 190 µL | 131 832 | 68 202 | 63 629 | 48 |
| Macaque serum (30551) | 190 µL | 48 674 | 17 418 | 31 256 | 64 |
| Means ± SD | — | — | — | — | 75.50 ± 13.08 |

Note:
$3.7 \times 10^{11}$ vg AAV8 have been grafted to the supports.

The differences between the treatment with and that without formaldehyde are not significant, although for all samples, the retention of anti-AAV8 antibodies by the non-crosslinked AAV8 column was higher than for the AAV8 column treated with formaldehyde (Table 1, FIG. 1).

Based on this observation as well as on the fact that the reuse of the columns was possible for both columns without tendency of loss of functionality over several tests, the use of columns without treatment by formaldehyde was preferred. A further reason to use a column prepared without formaldehyde treatment was the fact that the formaldehyde treatment takes about 2 weeks (at 4° C.).

NHS-Sepharose:

Although sepharose based chromatography gels are compressible which is not optimal when moving to large scale, we have also included such support because of several reasons: i) plasmapheresis columns, for instance, for removal of immunoglobulins are based on sepharose (e.g. Miltenyi), ii) the immobilization chemistry as proposed by GE HealthCare is rather fast in contrary to the epoxy chemistry, which is not only of advantage for the speed of the grafting procedure, but also for the integrity of the AAV particles to be grafted, and iii) in contrast to the Poros EPO support, the ligand density is known for NHS-sepharose (10 µmol ligand/ml gel).

In a preliminary experiment, a column of a nominal volume of 5 ml to which $3.4 \times 10^{12}$ vg AAV8 had been grafted was used in numerous succeeding runs using non-optimized conditions (flow rate: 0.25 ml/min=0.05 CV/min, IvIg load: 36 mg (=1 ml of IvIg)). 2 runs are presented in FIG. 2 with respect to the removal of anti-AAV8 antibodies. The runs were reproducible and satisfying as only 23-13% of anti-AAV8 antibodies in the IvIg preparation were not retained, meaning that as high as 73-83% (78±7.07%) of the loaded antibodies were retained thanks to the implemented column.

This was the start for performing several optimizations with respect to flow rate which impacts the time of interaction between the anti-AAV8 antibody and the grafted AAV8 particles, maximal loading capacity, etc.

Flow rate: a parameter susceptible of optimization for performing affinity chromatography is the flow rate and, directly associated with this, the time of contact between the antigen (here: the immobilized AAV8 particles serving as ligand) and the antibody (here: the target compound=anti-AAV8 antibody contained in the IvIg preparation which has to be removed). Thus in the case of the development of the NHS-sepharose based affinity system for removing anti-AAV8 antibodies the flow rate because impacting the dynamic binding capacity may be optimized for a given ligand density per ml of chromatography support.

In this context, the flow rate was varied between 0.1 and 0.5 ml/min (0.02-0.1 CV/min) and the results reported in FIG. 3 confirm that the reduction in the flow rate to 0.1 ml/min led to a higher anti-AAV8 removal (about 80%) in comparison to the flow rate of 0.5 ml/min (anti-AAV8 removal: about 60%).

Retention/removal of anti-AAV8 antibodies: each chromatographic column has a maximal dynamic capacity which was briefly evaluated by charging different volumes/quantities of IvIg to a 5 ml AAV8-NHS-sepharose column. For a 5 ml AAV8 column (NHS-sepharose) grafted with $3.4 \times 10^{12}$ vector genomes it could be established that at a flow rate of 0.1 ml/min (=0.02 CV/min) the maximum anti-AAV8 antibody retention was observed at the loading of about 35 mg of IvIg (FIG. 4) with significantly reduced retention at lower antibody loadings and a decreasing tendency at higher antibody loadings. In the case of the doubling of the column volume (use of two serially coupled columns), the maximal retention capacity at 0.1 ml/min could be increased from about 58% to about 81% at a loading of 70 mg IvIg (not shown).

Another way to increase the total retention (or removal) of anti-AAV8 antibodies consists in reloading of the flow-through in order to retain a supplementary amount of anti-AAV8 antibodies. In the first run, 55550 ng of anti-AAV8 antibodies (=1 mL of an IvIg preparation) were loaded onto a 5 ml AAV8-column. The flow through fractions of the first run containing 5065 ng of anti-AAV8 antibodies (=about 9% of the total loading) was reloaded onto the same column and the flow through containing about 2600 ng of antibodies, thus allowing a further retention of about 50% of the anti-AAV8 antibodies which had not been retained in the first round. The supplementary loadings of these flow throughs (runs 3 and 4) did not add on very much: for runs 3 and 4, only 0.9% and 0.1%, respectively, were retained when relating the amount to the initial loading. This signifies that the four loading rounds allowed altogether a supplementary removal of 3048 ng of antibodies (=5.5% of the amount initially loaded). About 3.6% (2017 ng) remained in the initial IvIg preparation.

Variation of the Amount of Grafted AAV8 Particles (FIG. 5):

Though the flow rate as well as the column volume can be used as parameter for increasing the overall capacity of the column, the density of the ligand (here vg of grafted AAV8 particles per column volume) is of equal importance. In this context, in addition to the medium ligand density of about $1.1 \times 10^{13}$ vg/column (see above) two different ligand densities were evaluated: $9.3 \times 10^{11}$ vg ('under-capacity') and $6.0 \times 10^{13}$ vg ('over-capacity'). The loading of 72 mg IvIg or 2 ml of positive anti-AAV8 human plasma to these columns led to the results, that for sample types the 'over-capacity' column increased the retention of anti-AAV8 antibodies (98% and 93%, respectively, for the plasma and the IVIG samples) whereas in the case of the 'under-capacity' column, retention efficacy was reduced to 45% and 70%, respectively. Thus, for optimal anti-AAV8 removal, AAV8 columns with a higher ligand density should be preferred.

Comparison of the Use of Full and Empty AAV Vector Particles:

Though for research purposes full AAV particles (=particles containing a vector genome) should be used because of the ease of the detection of leakage by using the very sensitive qPCR method, under clinical conditions, the use of empty AAV particles (=virus like particles or VLPs) could be preferred, mainly due to safety considerations.

In order to test the interest of the use of empty AAV particles, we have grafted equivalent quantities of full and empty AAV8 particles to NHS-sepharose ($2 \times 10^{12}$ vg—equivalent) and have performed succeeding runs loading 36 mg IvIg or 72 mg IvIg. The unexpected result obtained was the fact that the affinity column prepared with empty AAV8 particles showed a much higher retention/removal of anti-AAV8 antibodies (in the range of 50-55% for the column grafted with $2 \times 10^{12}$ particles) whereas the column to which full AAV8 particles had been grafted the removal efficiency was only in the range of 29-31% (FIG. 6A).

In this context, we have also evaluated the repeated use of the columns grafted with full and empty AAV8 particles in view of assessing their separation features over several cycles of use and regeneration. The results are presented in FIG. 6B.

Whereas for the column grafted with full AAV8 particles, there was no inactivation/degradation of the retention capacity of anti-AAV8 antibodies, meaning that a repeated use without loss of retention capacity is possible, we have seen a reduced retention capacity, in particular, for the column grafted with the lower amount of empty AAV8 particles which followed a logarithmic trend line ($y=-24.39 \ln(x)+96.094$) with an $R^2=0.9188$. The column grafted with a more elevated amount of empty AAV8 capsids ($3.2 \times 10^{13}$ vg-equivalent) showed a much-reduced loss in the retention capacity than the column grafted with $2 \times 10^{12}$ vg-equivalent of empty AAV8 particles.

This observation signifies that the repeated use of an AAV8 column generated using empty particles shows a reduction in the retention capacity for anti-AAV8 antibodies which is not seen when using full particles. Furthermore, the comparison of columns generated with different amounts of empty AAV8 particles indicates that in the case of the column to which lower amounts of AAV8 particles have been grafted the overall capacity is constantly reduced whereas for the column generated with about 10 times more particles the capacity is still sufficient for removing 80-90% of the anti-AAV8 antibodies even after several cycles of use.

In this case, the amount of grafted empty AAV8 particles was sufficient for the intended use, whereas for the column grafted with the lower amount of AAV8 particles, already at the first the removal is below 80%.

Thus, for clinical use in a plasmapheresis setting, columns with empty AAV particles can be used which has the additional advantage of using only a VLP and not a viral particle containing vector DNA. However, in the case of more than one cycle of use, it is preferable to use columns with a higher amount of grafted AAV8 particles.

Evaluation of AAV8 Columns for the Removal of Anti-AAV8 Antibodies from Human Plasma Samples:

IVIG as model system is rather artificial because this is a concentrated immunoglobulin preparation with very high antibody titers not found in classical animal or human plasma samples. Thus, in order to show the interest of the use of AAV-affinity columns for the removal of anti-AAV antibodies from plasma samples, we have also evaluated different plasma samples for the removal of anti-AAV8 antibodies.

FIG. 7A presents the retention results obtained for the loading of different volumes (range: 0.5-5 ml) of three different plasma samples with very different anti-AAV8 titers, ranging from 1/3 over 1/270 up to 1/7290, to a 5 ml AAV8-NHS-sepharose column to which $6.0 \times 10^{13}$ vg of AAV8 vector had been grafted. FIG. 7B presents the example of the removal of anti-AAV8 antibodies from a high tittering human plasma sample (1/7290). One ml of this plasma sample was loaded to the anti-AAV8 column and about 98% of the present anti-AAV8 could be retained and only about 2% were found in the flow through. Whereas for the plasma samples, except for one outlier, between 95 and 100% of the anti-AAV8 antibodies could be retained independently of the determined anti-AAV8 titers in the plasma samples, the retention of anti-AAV8 antibodies for the IvIg samples was much lower. In the case of loading 36 mg IvIg and 72 mg IvIg, the retentions were 63.5±9.2% and 84.0±12.7%, respectively, which is considerably lower than in the case of using plasma samples.

In the same time at least 22 succeeding runs with the same efficiency can be performed on an AAV-NHS-column when using full particles (FIG. 7A).

When using a column to which a low amount of AAV8 particles ($9.3 \times 10^{11}$ vg) had been grafted, 47% and 41% of anti-AAV8 antibodies, respectively were retained when loading 1 ml and 5 ml of a high anti-AAV8 antibody tittering plasma, thus confirming that a column with a higher level of grafted AAV8 particles has also a higher retention/removal capacity (see FIG. 5). Of course, such several columns grafted with low amounts of AAV8 particles may be serially used to greatly improve antibody retention since almost half of the anti-AAV8 antibodies was depleted using only one column.

Evaluation of AAV8 Columns for the Removal of Anti-AAV8 Antibodies from Human and Animal Serum Samples:

The ultimate aim is to remove anti-AAV8 antibodies from human serum, or in a model approach from animal sera. In order to assess the usefulness of an AAV8 column for the (entire) removal anti-AAV8 antibodies, 350 µl of human serum ('DRI' with an anti-AAV8 antibody level of about 3800 ng and neutralizing antibody titer of 1/316) have been loaded onto a 5 ml AAV8-NHS sepharose column to which $1.1 \times 10^{13}$ vg had been grafted. The passage of the human serum over the column led to the retention of 75% of anti-AAV8 antibodies (FIG. 9A), a complete flow through of total human immunoglobulin (FIG. 9B) and practical absence of neutralizing antibodies in all fractions (Table 2).

TABLE 2

Comparison of 4 different sera (human, dog, macaque) with respect to removal of anti-AAV8 antibodies, total immunoglobulin and AAV8 neutralizing antibodies (*).

|  | Human serum (DRI) Adult donor seropositive for AAV8 | Dog serum (Gothic) Dog dosed with an AAV8 vector | Macaque serum (TIM) Macaque dosed with an AAV8 vector | | Macaque serum (30551) Macaque naturally seropositive for AAV8 |
|---|---|---|---|---|---|
| Anti-AAV8 antibody titer | 1/2 430 | 1/65 610 | 1/590 490 | | 1/196 830 |
| Initial NAB titer | 1/200 | 1/158 000 | 1/204 800 | | 1/50 000 |
| Loading | 350 µl | 350 µl | 350 µl | 100 µl | 350 µl |
| Retention/removal of anti-AAV8 antibodies | 75% | 90% | 58% (**) | 92% | 86% |
| Passage/flow through of total immunoglobulin (***) | Complete | 9% retained | complete | ND | complete |
| Reduction factor of NAB | 160× | 5000× | ND | ND | 16000× |

Note:
(*) a 5 ml AAV8-NHS sepharose column was used grafted with $1.1 \times 10^{13}$ vg AAV8;
(**) even in the case of reloading of the flow through onto the same column ('cycling'), no further retention could be achieved signifying, that the maximal capacity of the column had been reached;
(***) flow through of total immunoglobulin without the retained anti-AAV8 antibodies;
ND not done.

Furthermore, one dog serum (Gothic) and two macaque sera (TIM, 30551) were also assessed. Their characteristics are presented in Table 2.

Related to the initial anti-AAV8 levels in the sera, the efficiency of removal/retention of anti-AAV8 antibodies was better or worse, with the best retention for the serum with the lowest anti-AAV8 concentration (dog serum Gothic, and the macaque serum 30551), whereas for the high titer macaque serum (TIM), the removal was 58% because of the very high anti-AAV8 levels caused by re-injection of AAV8 into the animal. When loading a reduced serum volume in the case of the macaque serum (TIM), the retention could be increased to 92%, signifying that the sample volume should be adapted to the column capacity or vice versa, the column volume should be adapted to the anti-AAV8 titer in the serum to be treated (Table 2).

With respect to the flow through of the total immunoglobulin, the retention was low (max: 9% for the dog serum) or non-detectable (human and macaque serum). Since the neutralizing antibody (NAB) titer is of importance and can be critical in the case the AAV vector particles are injected into patients positive for NAB the NAB titer has also to be reduced by the passage of the serum sample over the AAV8 column. In the cases of the human and the dog serum, the reduction factors were 160× and 5000×, respectively, showing clearly that the AAV8 column has also the capacity to remove specific neutralizing antibodies (Table 2).

In Vivo Evaluation of Anti-AAV8 Antibody Positive Human Plasma After Treatment with an AAV8 Immunoaffinity Column:

The final proof of concept (in a preclinical setting) is the evaluation of the efficiency of the removal of anti-AAV8 antibodies from human plasma followed by the injection of the treated plasma with respect to the untreated plasma and the assessment of their effects on the transduction efficiency of systemically injected AAV8 one day after administration of the plasma samples to be tested. The model system used was the injection of AAV8-human factor IX at a dose of $5\times10^{10}$ vg per mouse into mice which had been treated with the plasma to be tested (150 µl per mouse). The protocol used is presented in FIG. 10. As negative reference PBS was used.

5 ml of human plasma (1/7290) was passed through a 5 ml AAV8 NHS-sepharose column ($6\times10^{13}$ vg grafted) and the fractions were analyzed for anti-AAV8 antibodies (FIG. 11A) as well as for total immunoglobulin (FIG. 11B). Most of the anti-AAV8 antibodies (95%) were retained by the AAV8-column and only a small percentage was found in the flow through (5%) whereas in the case of the total immunoglobulin most of them (99%) were found in the flow through. Flow through (=the treated plasma sample mainly devoid of anti-AAV8 antibodies) fractions were pooled as well as the elution fractions (which were concentrated by a factor of 2) and these samples as well as the original non-treated human plasma sample and PBS as a negative control were injected. The neutralizing antibody titers of the four serum samples were as follows: 1/1000 (non-treated anti-AAV8 positive human plasma), <1/1 (anti-AAV8 positive human plasma after passage on the AAV8 column=preparation devoid of anti-AAV8 antibodies), 1/31.6 (eluted fractions using citrate buffer=the eluted anti-AAV8 antibodies originally contained in the human plasma and retained by the AAV8 column, concentrated 2-fold), <1/1 (PBS=negative for anti-AAV antibodies).

TABLE 3

In vivo evaluation of the efficiency of the removal of anti-AAV8 antibodies from human plasma.

| Serum preparation | Neutralizing anti-AAV8 antibody titer | Anti-AAV8 antibody titer | Immunoglobulin titer | Copy number of human factor IX gene, 21d* | Level of human factor IX in mouse serum (ng/ml), 14d |
|---|---|---|---|---|---|
| Human plasma sample positive for anti-AAV8 antibodies without treatment | 1:1000 | 230 000 ng/ml | 73 400 000 ng/ml | 0 | 0 |
| Pooled flow through (fractions A3-A8) of anti-AAV8 antibody positive human plasma sample | <1:1 | 400 ng/ml | 8 400 000 ng/ml | 7 | 142.73 |
| Pooled elution fractions positive for anti-AAV8 antibodies (B2-C3) | 1:31.6 | 4 200 ng/ml | 8 000 ng/ml | 3 | 42.05 |
| PBS | <1:1 | 0 | 0 | 5 | 96.95 |

Notes:
*the copy number was assessed with respect to the titin gene as reference.

The serum samples of the injected mice clearly showed that in the case of the mice injected with anti-AAV8 positive human plasma human anti-AAV8 antibodies were detectable at significant levels up to 7 days post-injection followed by a levelling down to levels found for all other mice. As expected the serum samples of mice treated with PBS or the pooled flow-through of the initially anti-AAV8 positive human plasma (which became negative after passage over the AAV8 column) were negative for human anti-AAV8 antibodies. NAb and IgG titers specific for AAV8 were detectable in the material eluted from the column (see Table 3), however, due to sample dilution during elution, the antibody titers measured in the elution material were lower to those in the original samples before column purification. Nevertheless, FIX transgene expression levels and vector genome copy number were maximal in mice preimmunized with the column flow through (negative for anti-AAV8 Ab), and significantly lower in animals preimmunized with the column elution material (positive for anti-AAV8 Ab). The overall results are presented in Table 3 and the detailed results with respect to anti-AAV8 antibodies found in the mouse sera at day 1 after sample injection are presented in Table 4.

TABLE 4

Anti-AAV8 antibodies detected in sera of mice treated with the three different serum preparations or PBS as negative control (see table 3) one day after injection/before injection of the AAV8 vector.

| Sample | Anti AAV8 levels (ng anti-AAV8 IgG/ml) at day 1 |
|---|---|
| Plasma | 3262 |
| FT | 27 |
| Elution | 190 |
| PBS | 17 |

The invention claimed is:

1. A method for removing anti-adeno-associated virus (AAV) antibodies, from a blood-derived composition comprising contacting said blood-derived composition with at least one support onto which is grafted one or more affinity ligand(s) that bind to anti-AAV antibodies, wherein at least one affinity ligand is an empty AAV-8 particle.

2. The method according to claim 1, wherein said composition is contacted with more than one support, wherein each support has grafted thereon different affinity ligands that bind to anti-AAV antibodies directed toward different AAV serotypes.

3. The method according to claim 1, wherein said affinity ligand binds to anti-AAV antibodies directed toward serotype AAV-1, -2, -3, -4, -5, -6, -7, -8, -9, -10, -11, -rh74 or engineered AAV capsid variants.

4. The method according to claim 1, said method comprising contacting the blood-derived composition with at least:
one support onto which is grafted an affinity ligand that binds to anti-AAV antibodies directed towards a first AAV serotype or onto which are grafted a set of affinity ligands that bind to anti-AAV antibodies directed towards said first AAV serotype; and
one support onto which is grafted an affinity ligand that binds to anti-AAV antibodies directed towards AAV-8 serotype, or onto which are grafted a set of affinity ligands that bind to anti-AAV antibodies directed towards AAV-8 serotype.

5. The method according to claim 1, said method comprising contacting the blood-derived composition with at least:
one support onto which is grafted an affinity ligand that binds to anti-AAV antibodies directed towards the AAV2 serotype or onto which are grafted a set of affinity ligands that bind to anti-AAV antibodies directed towards the AAV2 serotype; and
one support onto which is grafted an affinity ligand that binds to anti-AAV antibodies directed towards the AAV serotype, wherein said affinity ligand is an empty AAV-8 particle.

6. The method according to claim 1, wherein the blood-derived composition is whole blood, blood plasma, blood plasma fractions, blood plasma precipitate, blood plasma supernatant, solvent/detergent (SD) plasma, platelets, intravenous immunoglobulin (IVIG), IgM, purified coagulation factor concentrate, fibrinogen concentrate, or various other compositions which are derived from human or animal.

7. The method according to claim 1, wherein the blood-derived composition is whole blood or an IVIG composition.

8. The method according to claim 1, wherein the blood-derived composition is loaded several times onto the same support.

9. The method according to claim 1, wherein the blood-derived composition is loaded on several different columns serially arranged, either grafted with the same or different affinity ligand(s).

10. The method according to claim 1, wherein the blood-derived composition is loaded several times onto the same support and wherein said composition is loaded on several different columns serially arranged, either grafted with the same or different affinity ligand(s).

11. A support onto which are grafted one or more affinity ligand that bind to one or more anti-AAV antibody, respectively, wherein at least one affinity ligand is an empty AAV-8 particle.

12. The support according to claim 11, wherein said affinity ligand is:
a) an empty AAV particle;
b) a full AAV particle; or
c) a combination of empty and full AAV particles.

13. The support according to claim 11, grafted with:
an affinity ligand that binds to anti-AAV-8 antibodies wherein said affinity ligand is an empty AAV-8 particle, or
the first affinity ligand that binds to the anti-AAV-8 antibodies, wherein said first affinity ligand is an empty AAV-8 particle and the second affinity ligand that binds to the anti-AAV antibodies directed towards the second AAV serotype.

14. The support according to claim 11, grafted with:
the first affinity ligand that binds to the anti-AAV antibodies directed towards the AAV-8 serotype, wherein said first affinity ligand is an empty AAV-8 particle, and the second affinity ligand that binds to the anti-AAV antibodies directed towards the AAV2 serotype.

15. A method of treating a disease by gene therapy comprising:
administration to a subject in need of treatment an AAV vector that comprises a therapeutic gene of interest appropriate for the treatment of said disease, wherein said AAV vector is of a given serotype and said AAV vector is administered to the subject after a blood-derived composition which has been processed according to the method of claim 1 to remove from said composition anti-AAV antibodies that bind to said given serotype has been administered to said subject.

16. The method according to claim 15, wherein the blood-derived composition is whole blood or wherein the subject had previously undergone plasmapheresis and the blood-derived composition is an IVIG composition.

17. An extracorporeal device through which a patient's blood or plasma can be circulated prior to being returned to the patient, said device comprising a support according to claim 11.

* * * * *